United States Patent
Kepley

(10) Patent No.: US 6,203,516 B1
(45) Date of Patent: Mar. 20, 2001

(54) PHACOEMULSIFICATION DEVICE AND METHOD FOR USING DUAL LOOP FREQUENCY AND POWER CONTROL

(75) Inventor: Kevin Paul Kepley, Ballwin, MO (US)

(73) Assignee: Bausch & Lomb Surgical, Inc., Claremont, CA (US)

( * ) Notice: Subject to any disclaimer, the term of this patent is extended or adjusted under 35 U.S.C. 154(b) by 0 days.

(21) Appl. No.: 08/915,991

(22) Filed: Aug. 21, 1997

Related U.S. Application Data

(60) Provisional application No. 60/025,498, filed on Aug. 29, 1996.

(51) Int. Cl.[7] .............................. A61B 17/20; A61B 17/22
(52) U.S. Cl. ................................ 604/22; 606/38; 606/128
(58) Field of Search ......................... 604/20, 22; 606/34, 606/38, 127, 128, 107; 601/2; 310/316.01, 317; 323/282, 285; 702/64, 71, 72

(56) References Cited

U.S. PATENT DOCUMENTS

| | | | |
|---|---|---|---|
| 3,693,613 | 9/1972 | Kelman | 128/24 |
| 3,902,495 | 9/1975 | Weiss et al. | 128/276 |
| 3,990,452 | 11/1976 | Murry et al. | 128/305 |
| 4,180,074 | 12/1979 | Murry et al. | 128/176 |
| 4,188,927 | 2/1980 | Harris | 128/303 |
| 4,314,560 | 2/1982 | Helfgott et al. | 128/305 |
| 4,378,530 | 3/1983 | Garde | 330/297 |
| 4,428,748 | 1/1984 | Peyman et al. | 604/22 |
| 4,504,264 | 3/1985 | Kelman | 604/22 |
| 4,525,775 | 6/1985 | Eydelman | 364/148 |
| 4,587,958 | 5/1986 | Noguchi et al. | 128/24 |
| 4,793,345 | 12/1988 | Lehmer | 128/303 |
| 4,827,911 | 5/1989 | Broadwin et al. | 128/24 |
| 4,868,445 | 9/1989 | Wand | 310/316 |
| 4,933,843 | 6/1990 | Scheller | 364/413 |
| 5,042,460 | 8/1991 | Sakurai et al. | 128/24 |
| 5,112,300 | 5/1992 | Ureche | 604/22 |
| 5,121,023 | 6/1992 | Abel | 310/316 |
| 5,139,509 | 8/1992 | Fischer et al. | 606/107 |
| 5,151,085 | 9/1992 | Sakurai et al. | 604/22 |
| 5,220,272 | 6/1993 | Nelson | 323/282 |
| 5,331,951 | 7/1994 | Kepley | 601/4 |
| 5,370,602 | 12/1994 | Kepley | 601/2 |
| 5,388,569 | 2/1995 | Kepley | 601/2 |
| 5,406,503 | 4/1995 | Williams, Jr. et al. | 354/571 |
| 5,455,766 | 10/1995 | Scheller et al. | 364/413 |

*Primary Examiner*—Sharon Kennedy
*Assistant Examiner*—Michael J. Hayes
(74) *Attorney, Agent, or Firm*—Grant D. Kang

(57) ABSTRACT

The invention is an improved phacoemulsification probe drive circuit for supplying electrical power to an ultrasonic transducer. The drive circuit has a power control loop and a frequency control loop. The power control loop has a variable gain amplifier whose output is an input to a power amplifier. After the power amplifier amplifies power, power is delivered to a transformer and, thereafter, to a transducer. The voltage and current applied to the primary of the transformer are sensed to generate a signal proportional to the power (real or apparent) and the result is compared against a power command originating from a foot pedal. Once compared, the result of this comparison is sent to a first controller which acts upon the information by sending a corrective signal to the variable gain amplifier. Also, the phase of the voltage and current waveforms applied to the primary of the transformer are sensed by a phase detector. The phase angle is then derived and compared against a phase command which is determined from the initial calibration of the system. The summer/difference block sends its resulting comparison to a second controller which sends a control signal to the voltage controlled oscillator (VCO). The VCO receives the signal and sends a specific frequency at a fixed voltage to the variable gain amplifier.

3 Claims, 29 Drawing Sheets

Microfiche Appendix Included
(32 Microfiche, 6267 Pages)

PHACOEMULSIFICATION DEVICE AND METHOD FOR USING DUAL LOOP FREQUENCY AND POWER CONTROL

This application claims the benefit of Provisional Application No. 60/025,498, filed Aug. 29, 1996.

BACKGROUND OF THE INVENTION

MICROFICHE APPENDIX

This application includes a microfiche appendix consisting of 32 slides and 6,267 frames, which is a copy of the provisional application under which priority is claimed and updated source code.

1. Field of the Invention

This invention relates to phacoemulsification devices and, more particularly, to a method for controlling a phacoemulsification device.

2. Related Art

Ultrasonic probes have traditionally been used for phacoemulsification, namely, for rupturing of cataracts in the eye and for aspiration of the pieces of tissue disrupted. These ultrasonic probes must be carefully powered for proper operation. Operating the ultrasonic probe at its resonant frequency takes advantage of the resonant characteristics of the ultrasonic transducer. Resonance is defined as the phenomenon wherein a system is driven at or near one of its natural modes.

Accordingly, the prior art has focused on how to determine the resonant frequency of a transducer. Theoretically, this problem has been solved. A typical way of determining the resonant frequency of an ultrasonic transducer is to compare the phase angle between the voltage waveform applied to the ultrasonic transducer and the waveform of the current drawn by the transducer.

When voltage is applied to a circuit, current will flow through the circuit. When the voltage and current waveforms are viewed for a particular circuit, the current waveform will lag the voltage waveform if the circuit is inductive, and the voltage waveform will lag the current waveform if the circuit is capacitive. The time difference between the points when the current waveform and voltage waveform intersect the zero axis is measured in trigonometric terms by the phase angle $\Phi$. For purely resistive circuits, $\Phi$ equals zero and the voltage in the current waveforms are said to be in phase. For purely inductive circuits, $\Phi$ equals 90° and for purely capacitive circuits, $\Phi$ equals −90° and the voltage in the current waveforms are said to be out of phase.

The presence of an inductive or capacitive reactance component in a load impedance will decrease the efficiency of power delivery of the system since only resistive components can actually dissipate power.

For circuits containing all three elements, resistors, inductors and capacitors, there will be some frequencies where the total impedance of the circuit will appear purely resistive even though the circuit contains reactive elements, i.e., the resistive elements plus the imaginary component caused by the presence of the inductive and capacitive elements. These frequencies are at or near the resonant and/or anti-resonant frequencies.

Therefore, in theory, one method of determining the resonant frequencies of certain types of complex circuits is to apply an alternating voltage to the circuit and to vary the frequency until the phase angle $\Phi$ between the voltage and current is zero. The frequencies where this condition occurs are the actual resonant frequencies of that particular circuit. The resonant frequency is that frequency or frequencies at which the circuit response (i.e., admittance) is locally a maximum, and the anti-resonant frequency is that frequency or frequencies at which the response achieves a local minimum.

When driving a circuit having both resistive and reactive components, it is important to know the value of the phase angle $\Phi$ because the power delivered to a load is given by the following equation:

$$\text{Power} = VI \cos(\Phi)$$

where V is the voltage drop across the load impedance; I is the series current flowing through the load impedance; and cosine phi is the power factor of the circuit. Clearly, for a phase angle equal to zero, cosine (0) equals 1 and the transfer of power from the source to the circuit is at maximum. This situation exists where a purely resistive load exists.

As these theoretical principles are practically applied, problems have been encountered. Specifically, as environmental conditions such as temperature, time, etc., change, the characteristics of the probe changes. These changes are reflected as changes in the values of the various resistive and reactive components of the ultrasonic probe electrical model of FIG. 1. In other words, as the environmental factors change, the mechanical resonant frequency of ultrasonic probe changes also. To solve this problem, there has been a direction in the prior art to provide a phase locked circuit to ensure that the phase angle of the system, $\Phi$, will be zero, such as for example in U.S. Pat. Nos. 5,446,416; 5,210,509; 5,097,219; 5,072,195; 4,973,876; 4,484,154; and 4,114,110.

However, loading on the transducer will have a damping effect on the vibrations of the transducer. In other words, the load may dampen the vibrations of the transducer. When this condition occurs, the resonant frequency may change and phase angle $\Phi$ will longer be zero and the transfer of power will no longer be optimum. Therefore, unless provisions are made in the circuit to alter the phase angle $\Phi$, optimum power transfer cannot be achieved.

Accordingly, methods other than locking the phase angle $\Phi$ have been explored such as using a tunable inductor in a control system to cancel out the capacitive reactants of the load impedance presented by the ultrasonic transducer, such as that disclosed in U.S. Pat. Nos. 4,970,656; and 4,954,960. Alternatively, using the admittance of the ultrasonic transducer as the tuning parameter rather than the phase angle has also been explored in U.S. Pat. No. 5,431,664.

Approaching this problem from a purely output power standpoint has also been explored in U.S. Pat. No. 5,331,951 in which the actual electrical power supplied to the drive circuit is examined and the supply voltage is varied after comparing the electrical power supplied with the desired transducer power level. Tangentially, this patent also addresses a way to substantially minimize the power amplifier's power consumption by providing a boost regulator for supplying voltage to the amplifier.

In yet another approach, phase-regulated power and frequency control is utilized, such as in U.S. Pat. No. 4,849,872. Therein the initial resonance frequency of the ultrasonic transducer is determined and a capacitive phase angle between the voltage waveform and current waveform is introduced and maintained so that by phase control of the phase control circuit, the operating frequency of the oscillator is reduced relative to the series resonance frequency of the transducer. The phase angle is typically maintained as a non-zero constant. Similarly, in U.S. Pat. No. 4,888,565, a power control feedback loop for monitoring the output signal and a frequency control feedback loop are utilized to provide maximum current. This approach relies on holding the mains current constant.

An electrical model of a ultrasonic phacoemulsification probe in the vicinity of resonance is provided in FIG. 1. The model has a voltage source 1401 connected to a 1130 picofarad capacitor 1402 connected in parallel to a series RLC circuit 1403, wherein the resistor is 220 ohms, the inductor is 1.708 henrys, and the capacitor is 18 picofarads.

When examining the apparent power resulting from the electrical model, the graphs of FIGS. 2 and 3 are obtained. As seen in these Figures, the apparent power peaks at 28.661 kHz with a phase angle of approximately −42 degrees. This is expected due to the parallel capacitance in RLC circuit 1403.

When examining the real power resulting from the electrical model, the graphs of FIGS. 4 and 5 are obtained. As seen in these Figures, the real power peaks correctly at 28.7 kHz, but the phase angle is approximately −24.5 degrees.

When a compensating inductor with a calculated value of 27.21 millihenrys is placed in ghost block 1404 of FIG. 1 to cancel the reactive component of FIG. 1 and the resultant apparent power and real power information is obtained as in FIGS. 6 and 7, the apparent power and the real power now both correctly peak at 28.7 kHz with a phase of approximately −0.5 degrees. Thus, it can be seen that the inductor in ghost block 1404 compensates the parallel capacitance 1402 and makes the circuit appear resistive (zero phase) at resonance. From these graphs, it is clear that the real power provides a more accurate view of resonance frequency, unless a compensating inductor is added near resonance. Accordingly, resonant frequency is defined herein as the frequency at which real power achieves a (local) maximum. However, apparent power may be used to determine the resonant frequency if the parallel capacitance is compensated at resonance. Apparent power provides an approximation of resonant frequency (frequency at which the local maximum occurs) if a compensating inductor compensates parallel capacitance 1402 near resonance.

Therefore, there is a need in the art to maximize the power output to an ultrasonic transducer which is responsive to both environmental changes as well as changes in loading, and yet which also does not necessarily require a fixed phase angle or a constant current.

SUMMARY OF THE INVENTION

It is in the view of the above problems that the present invention was developed. The invention is an improved phacoemulsification probe drive circuit for supplying electrical power to an ultrasonic transducer. The drive circuit has a power control loop and a frequency control loop. The power control loop has a variable gain amplifier whose output is an input to a power amplifier. After the power amplifier amplifies power, power is delivered to a transformer and, thereafter, to a transducer. The voltage and current applied to the primary of the transformer are sensed to generate a signal proportional to the power (real or apparent) and the result is compared against a power command originating from a foot pedal. Once compared, the result of this comparison is sent to a first controller which acts upon the information by sending a corrective signal to the variable gain amplifier. Also, the phase of the voltage and current waveforms applied to the primary of the transformer are sensed by a phase detector. The phase angle is then derived and compared against a phase command which is determined from the initial calibration of the system. The summer/difference block sends its resulting comparison to a second controller which sends a control signal to the voltage controlled oscillator (VCO). The VCO receives the signal and sends a specific frequency at a fixed voltage to the variable gain amplifier.

Before operation, the phacoemulsification probe is calibrated by applying a constant voltage to the probe and sweeping the drive circuit through a series of frequencies. Then, a different voltage is selected and another frequency sweep is performed. This process is repeated for one or more voltage levels and the information on the power and phase versus frequency is stored in memory so that the optimal phase angle at resonance associated with a certain power requirement may be determined easily, although the phase angle may be relatively constant over a range of power levels. In addition, when the power and phase information is stored in memory, a range of frequencies about a certain resonant frequency is used to create a window beyond which certain frequencies may not be used.

In operation, a foot pedal is depressed providing a power command which is compared against the existing power. The difference between these two levels is transmitted to the power loop controller. Acting upon the information stored in memory, the power loop controller selects the appropriate voltage level necessary to correct the difference between the power and the power command and sends this information to the control input of the variable gain amplifier. The variable gain amplifier sends its output to a power amplifier. The output of the power amplifier is applied to the transformer and simultaneously to both the power monitor and the phase detector. The power is then calculated and compared against the power command signal received from the foot control and the power loop begins again. The phase detector sends its phase information to a summer/difference block which compares the actual phase against a calculated phase command. The difference between the phase command and the existing phase is then sent to the frequency loop controller which communicates a signal to the voltage controlled oscillator to emit a certain frequency to the input of the variable gain amplifier which completes the frequency loop. The phase command is determined from the information taken at calibration time and from the current power command.

Further features and advantages of the present invention, as well as the structure and operation of various embodiments of the present invention, are described below in detail with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENTS

Figure 1:
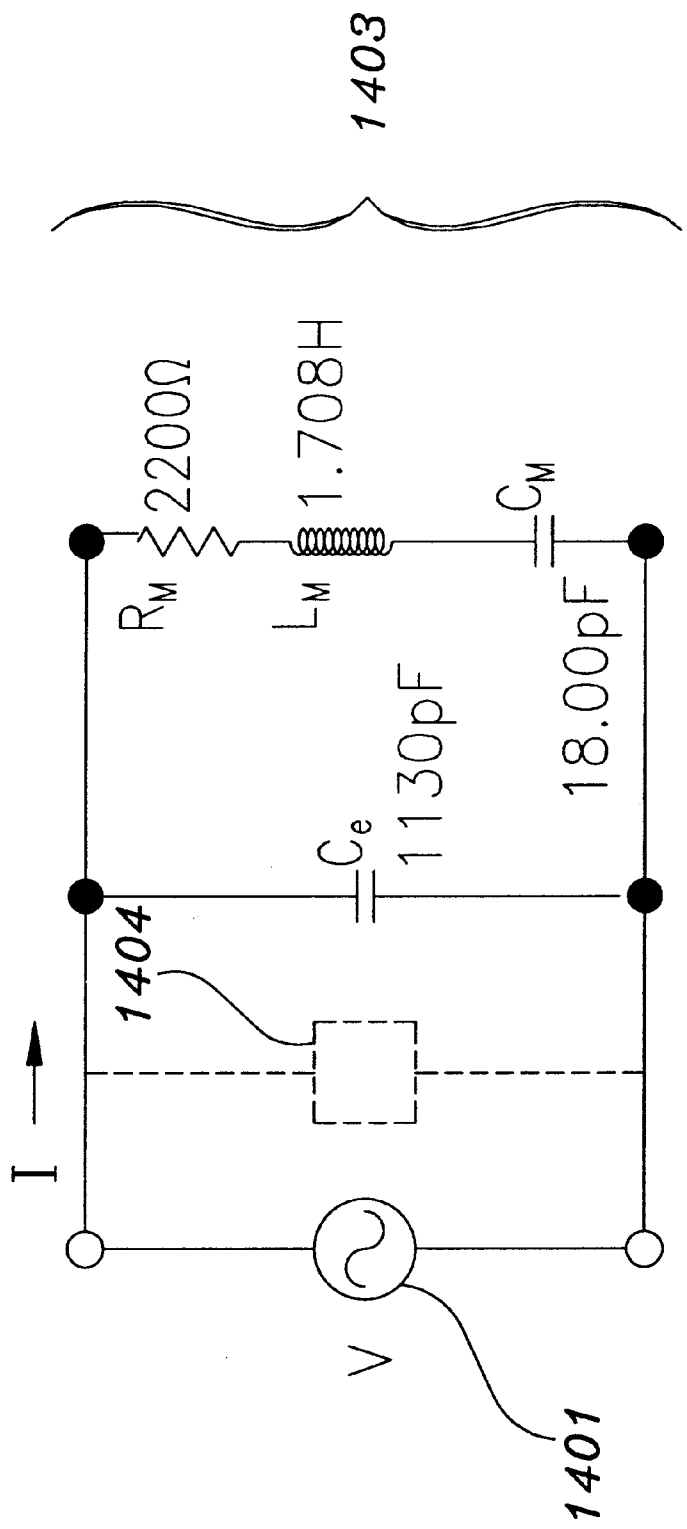
FIG. 1 illustrates a block diagram of an electrical model of an ultrasonic phacoemulsification probe operating near its resonance frequency.
Figure 2:
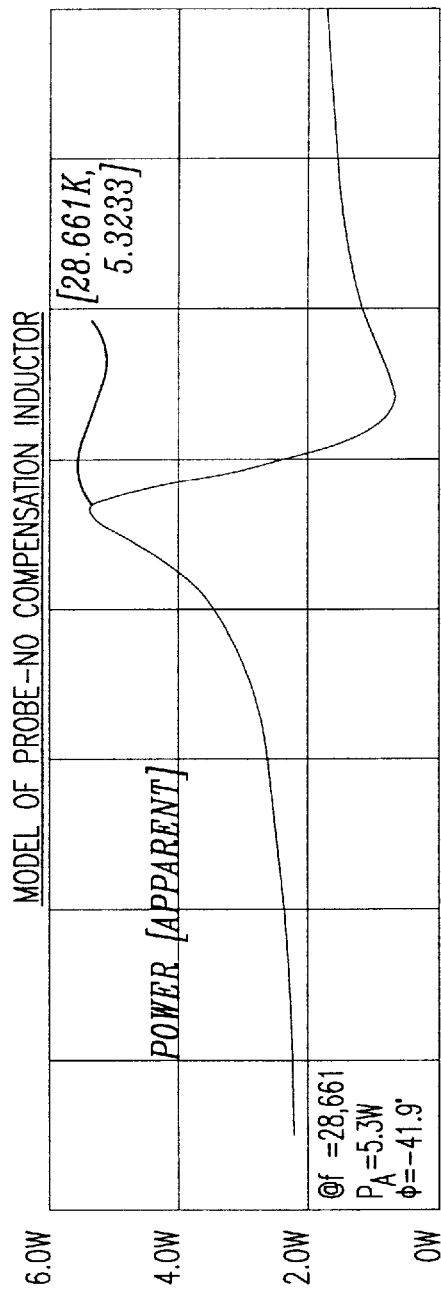
FIG. 2 is a graph of apparent power in accordance with the electrical model of FIG. 1.
Figure 3:
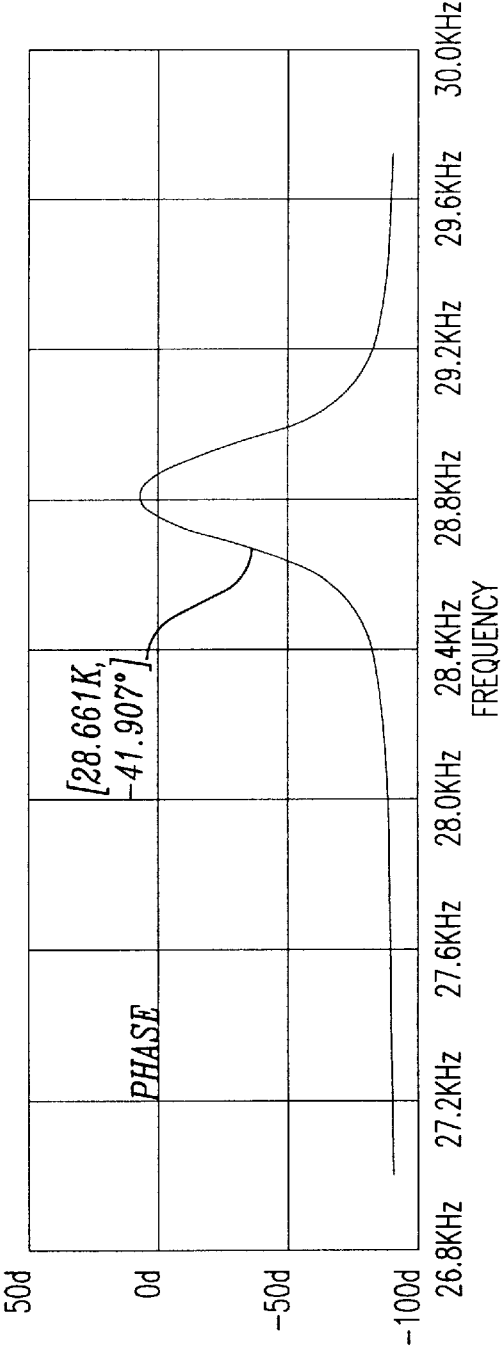
FIG. 3 is a graph of the phase angle between the voltage and current waveforms relating to the apparent power graph of FIG. 2 and resulting from the electrical model of FIG. 1.
Figure 4:
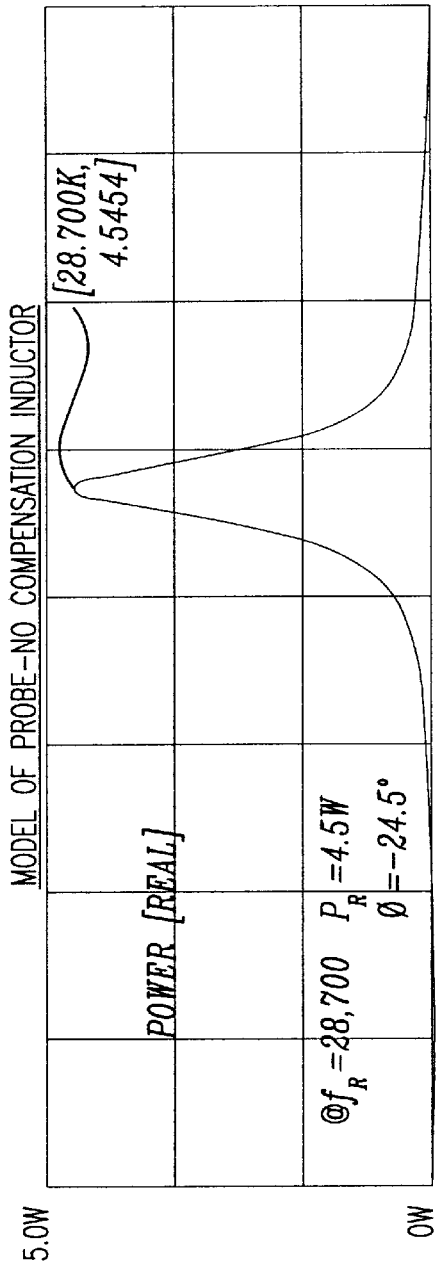
FIG. 4 is a graph of real power in accordance with the electrical model of FIG. 1.
Figure 5:
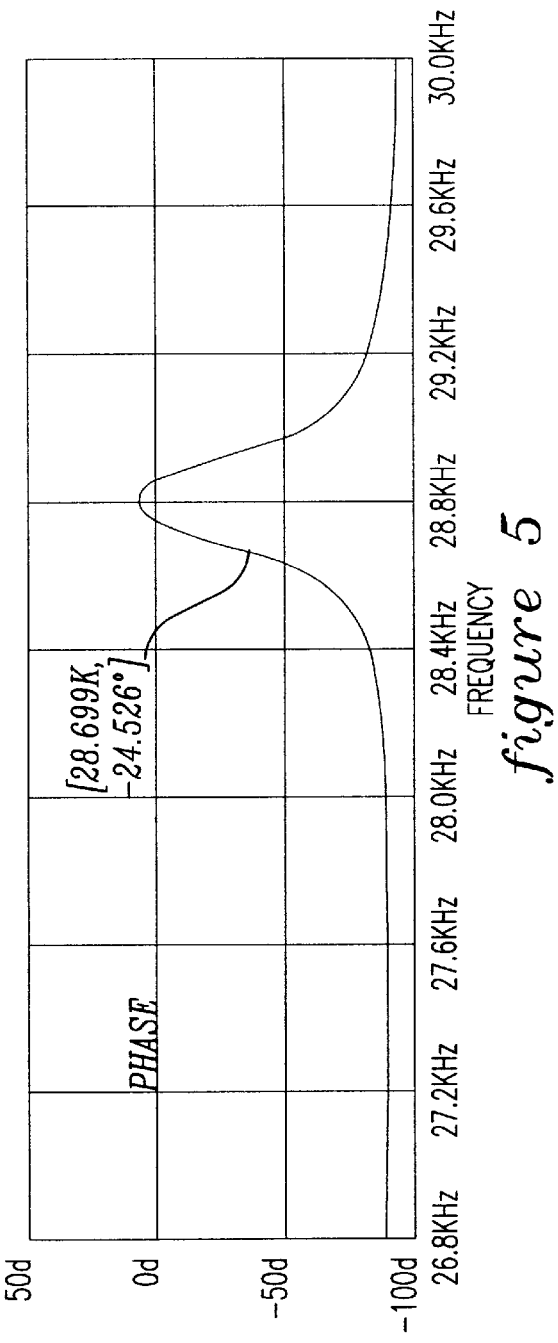
FIG. 5 is a graph of the phase angle between the voltage and current waveforms relating to the real power graph of FIG. 4 and resulting from the electrical model of FIG. 1.
Figure 6:
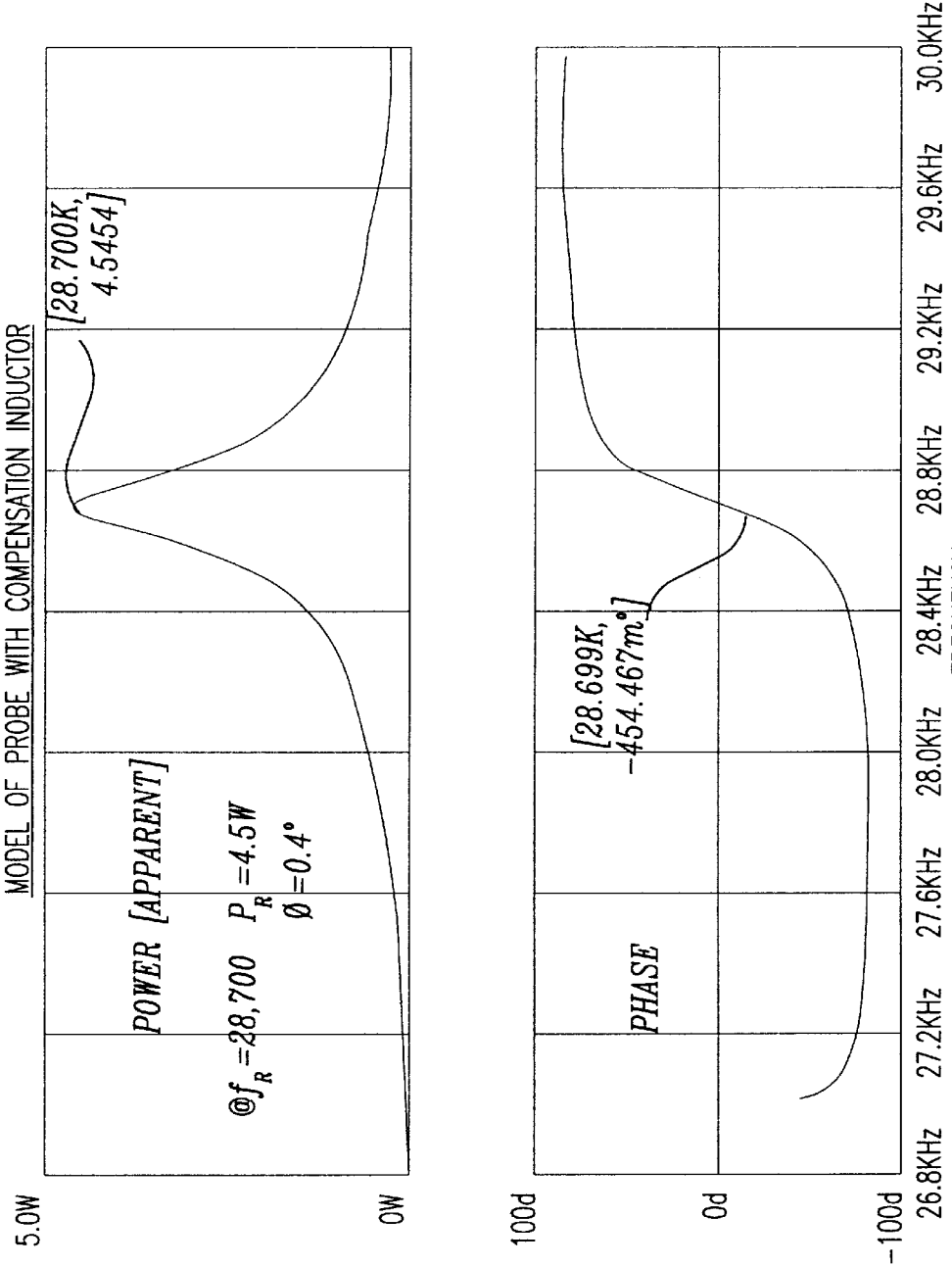
FIG. 6 is a graph of apparent power and phase angle with the addition of a compensating inductor to the electrical model of FIG. 5.
Figure 7:
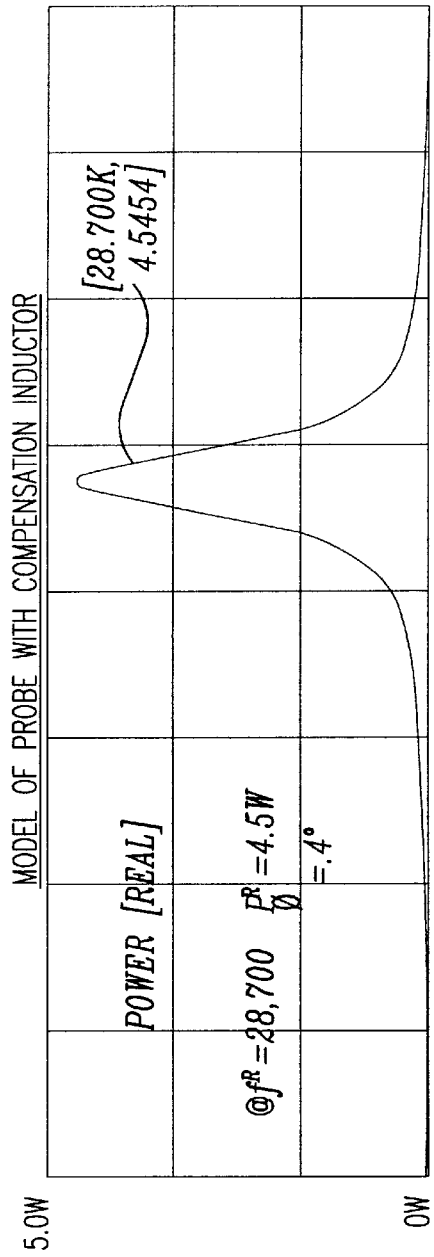
FIG. 7 is a graph of real power and phase angle with the addition of a compensating inductor to the electrical model of FIG. 5.
Figure 7:
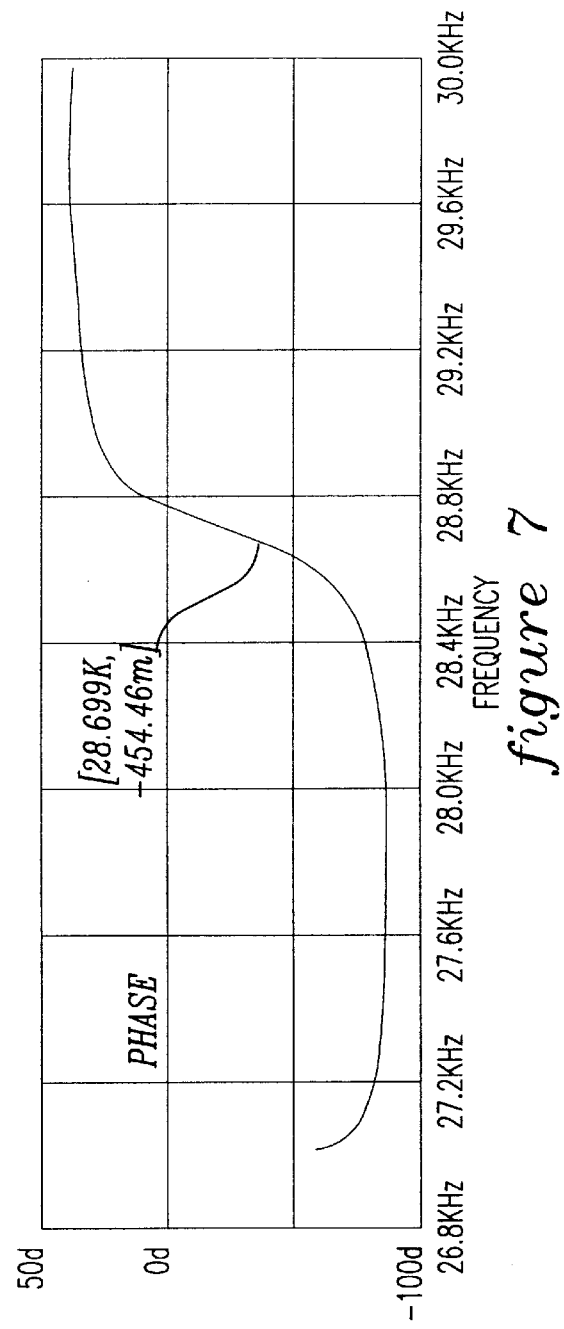
Figure 8:
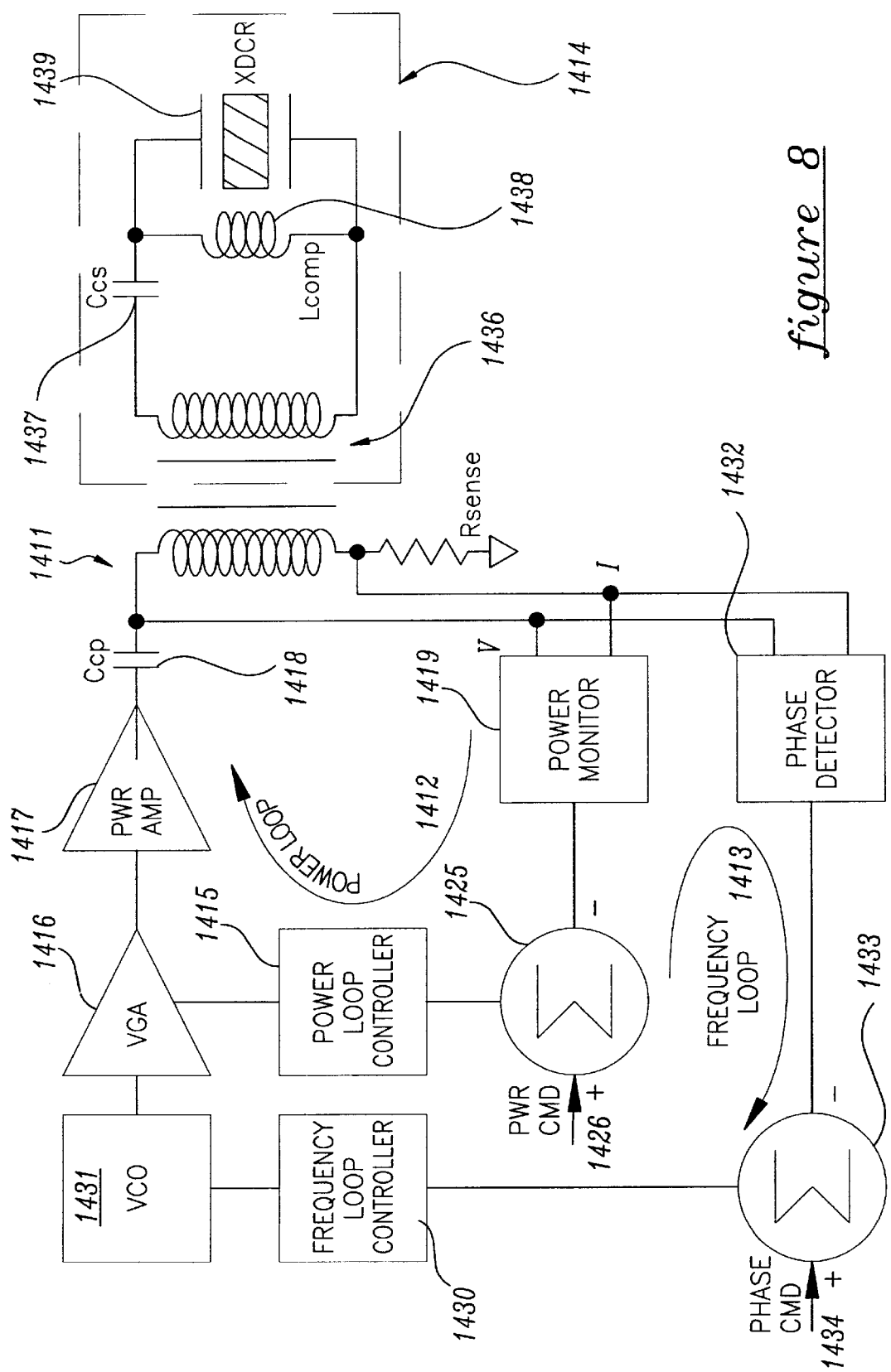
FIG. 8 illustrates a block diagram of the phacoemulsification probe system of the present invention.

Referring to the accompanying drawings in which like reference numbers indicate like elements, FIG. 8 shows the phacoemulsification probe system, shown generally at 1411, of the present invention. Phacoemulsification probe system 1411 comprises power loop shown generally at 1412, frequency loop shown generally at 1413, and isolated transducer circuit shown generally at 1414.

As shown in FIG. 8, power loop 1412 comprises power loop controller 1415, variable gain amplifier 1416, power amplifier 1417, first coupling capacitor 1418, transformer 1436, power monitor 1419, first summer/difference block 1425, and power command signal input 1426.

Power loop controller 1415 has an output to variable gain amplifier 1416. The function of power loop controller 1415 is twofold: (1) a perform a square root operation (power is proportional to the square of the voltage); and (2) to ensure loop stability and ensure desired system response characteristics. Optionally, the power loop controller 1415 can store in memory peak power information, although this can also be handled by a coprocessor and coprocessor memory combination. Power amplifier 1417 receives an input from the output of variable gain amplifier 1416. The output from power amplifier 1417 proceeds through coupling capacitor 1418 which compensates for leakage inductance as well as blocks any direct current from power amplifier 1417. Power is then delivered to primary transformer 1436 and thence to isolated transducer circuit 1414. In addition, the voltage and current applied to the isolated transducer circuit 1414 are sensed by power monitor 1419. Power monitor 1419 generates a signal proportional to the power (real or apparent).

Figure 9:
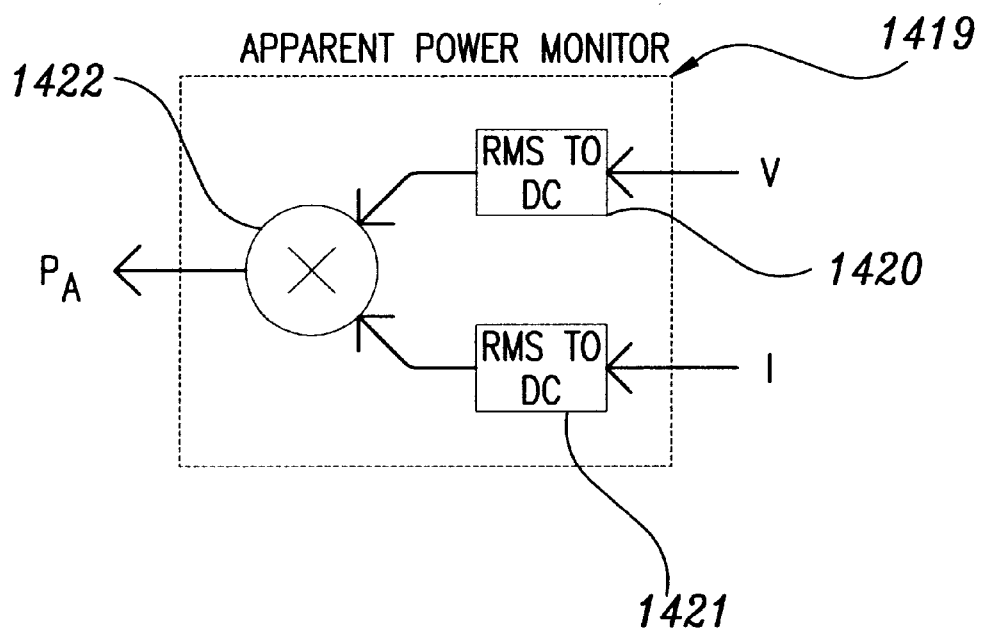
FIG. 9 illustrates a more detailed apparent power block diagram of the power monitor block in FIG. 8.
Figure 10:
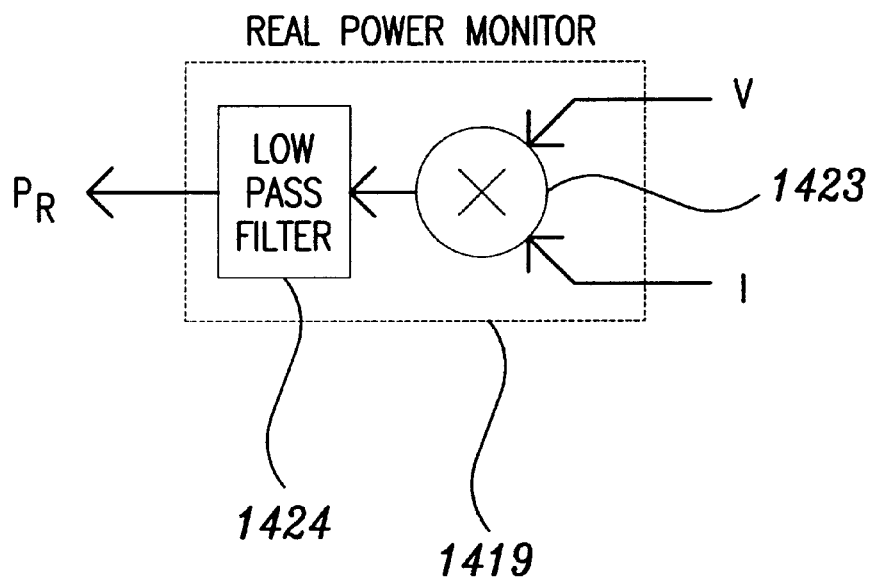
FIG. 10 illustrates a more detailed real power block diagram of the power monitor block in FIG. 8.

As shown in FIG. 9, power monitor 1419 may be an apparent power monitor which comprises a voltage root mean square (RMS) to DC converter 1420, current RMS to DC converter 1421, and multiplier 1422. A DC signal providing an apparent power value is produced which is then communicated to first summer/difference block 1425. Alternatively, power monitor 1419 may be a real power monitor which comprises a voltage and current multiplier 1423 connected to low pass filter 1424. A real power value is produced with is then communicated to first summer/difference block 1425.

First summer/difference block 1425 compares the power level detected by power monitor 1419 and the power command provided at power command signal input 1426. In hardware, any summer/difference block discussed herein may be embodied as a difference amplifier, and in software is commonly referred to as a "subtraction" operation. The results of the comparison are communicated to power loop controller 1415. A calculation is made on the magnitude of correction required, and power loop controller 1415 sends a new signal to voltage gain amplifier 1416 based on the calculation. The calculation may be performed by power loop controller 1415, or any other component associated with power loop controller 1415 such as a coprocessor and coprocessor memory. This completes one round of power loop 1412.

Frequency loop 1413 comprises frequency loop controller 1430 which communicates a signal to voltage controlled oscillator 1431 which itself provides an input to variable gain amplifier 1416, thence to power amplifier 1417, through coupling capacitor 1418, to isolated transducer circuit 1414. The phase of the voltage and current waveforms applied to the isolated transducer circuit 1414 are sensed by phase detector 1432 and then communicated to second summer/difference block 1433. A phase command which is determined from the initial calibration of the system and possibly from subsequent calculation is also communicated to phase command input 1434 of second summer/difference block 1433. Thereafter, second summer/difference block 1433 communicates an error signal based on the phase difference between the actual phase and the phase command to frequency loop controller 1430. A calculation is made on the magnitude of correction required, and frequency loop controller 1430 sends a new signal to voltage controlled oscillator 1431 based on the calculation. The calculation may be performed by frequency loop controller 1430, or any other component associated with power loop controller 1430 such as a coprocessor and coprocessor memory. This completes one iteration of frequency loop 1413.

Turning now to isolated transducer circuit 1414, isolated transducer circuit 1414 comprises isolating secondary transformer 1436, second coupling capacitor 1437, compensating inductor 1438, and ultrasonic transducer 1439. More specifically, the parallel combination of ultrasonic transducer 1439 and compensating inductor 1438 is connected in series with the secondary of transformer 1436 and coupling capacitor 1437. The function of second coupling capacitor 1437 is to compensate for any leakage inductance from isolating secondary transformer 1436.

The value of compensating inductor 1438 is selected so that the magnitude of its reactance equals the magnitude of the reactance (C) of the parallel capacitance of ultrasonic transducer 1439. If F represents the resonant frequency of the ultrasonic transducer, then the proper value of inductance to compensate the ultrasonic transducer is one divided by the quantity of the square of the quantity of two times pi times F, end quantity, times C, end quantity. In calculating the value of compensating inductor 1438, it is commonly known that the values for ultrasonic transducer 1439 experience some amount of variation. Accordingly, a sampling of ultrasonic transducer 1439 parts can be made to derive the average value of parallel capacitance and thus to calculate the value of compensating inductor 1438. Because compensating inductor 1438 is a fixed value, it is known that this circuit is designed to provide for a relatively accurate inductor value to make phacoemulsification probe system 1401 appear to be purely resistive with the parallel combination of ultrasonic transducer 1439 and compensating inductor 1438, with a small degree of error which is compensated by using power loop 1412 and frequency loop 1413 in combination.

The phacoemulsification probe system 1411 has two separate and distinct modes. One mode is calibration in which the control loops are opened, and the summer/difference blocks, 1425 and 1433 respectively, are removed, and the other is operation in which the control loops are closed so that a response may be given to a power command from a footpedal.

Turning to the operation of phacoemulsification probe system 1411, prior to actual surgical use, a calibration of the entire system 1411 must first be provided. The purpose of the calibration step is to initialize a window of voltages and frequencies of operation of phacoemulsification probe system 1411.

Briefly, the purpose of calibration is to find an operational window of voltages and frequencies by successively iterating a series of frequencies at a constant voltage (sweeping the frequency), and then possibly repeating this for different voltages to derive the resonant frequency at various power levels. This information is stored in memory and then is used to determine the phase commands in the control of the dual loop phacoemulsification probe system 1411.

Calibration is initiated by a request from the user. As a general overview, calibration consists of one or more frequency sweeps. The frequency is swept from a lower starting frequency to a higher end frequency by frequency loop controller 1430. During this frequency sweep, the excitation level is kept constant by power loop controller 1415. On a more detailed level, a command signal to calibrate is received by power loop controller 1415 and frequency loop controller 1427. Power loop controller 1415 then sends a command signal to variable gain amplifier 1416 such that variable gain amplifier will output a fixed voltage. Similarly, frequency loop controller 1430 sends a signal to voltage controlled oscillator 1431. Upon receipt of the signal from frequency loop controller 1430, voltage controlled oscillator 1431 transmits a frequency sweep to variable gain amplifier 1416. Variable gain amplifier 1416 applies a voltage gain to the frequency sweep voltage to produce an output voltage. This output voltage is communicated as an input voltage to power amplifier 1417. Power amplifier 1417 amplifies the power and delivers the power to isolating secondary transformer 1436 via coupling capacitor 1418 (the operation of which was discussed previously). Power monitor 1419 determines the frequency at which peak power achieves a local maximum, and phase detector 1432 determines the frequency where the phase crosses zero. A window of operating frequencies is then determined about this critical frequency. The back end of the window is determined by first determining where the frequency achieves a local maximum peak power as well as a proximity to a zero phase angle crossing. From this area, the frequency sweep is examined at lower frequencies to determine the frequency at which a prior zero phase angle crossing occurred. From the frequency of this prior zero phase angle crossing, a fixed frequency amount is added to establish the back end of the operating frequency window. The forward end of the operating frequency window may be established in a similar way. Alternatively, a fixed frequency band such a 1 kHz may be established backward and forward of the critical frequency. The purpose of establishing a operational frequency window is to ensure that the resonant frequency will occur within the operational frequency window, without encountering other zero phase crossings. Information on peak power, phase of peak power, operating power level, and the frequency window may be stored in memory.

It should be noted that it may be preferable to conduct a coarse frequency sweep to identify the general areas of interest, and then to conduct a finer frequency sweep to focus on the general area of interest. In this way, memory requirements are minimized, as the sweep information stored in memory is larger, but exists only temporarily to permit derivation of the window information, whereas the window information is relatively more permanent, but lesser in memory space requirements.

After sweeping the frequency, power loop controller 1415 changes the voltage gain and a different voltage (power/excitation level) is utilized to sweep the frequency, the phase and power information resulting therefrom being stored in memory. This data taken during calibration allows determination of varying phase angles so that a phase command may be determined during subsequent operation based upon the error signals derived from first summer/difference block 1425 and second summer/difference block 1433 during operation of the phacoemulsification probe system 1411.

After the calibration of phacoemulsification probe system 1411 is completed, a process which may take between four to six seconds, the actual operation of phacoemulsification probe system 1411 as a phacoemulsification handpiece may commence. In operation, the surgeon depresses a foot pedal (not shown) which sends a power command to power command signal input 1426 of first summer/difference block 1425. Based on the difference between the new power command and the existing power level of the system, first summer/difference block 1425 sends an error signal to power loop controller 1415.

Power loop controller 1415 computes a new voltage requirement and sends a signal to variable gain amplifier 1416. Similarly, a phase command signal determined from the power command and the information stored during calibration enters phase command signal input 1434 to second summer/difference block 1433. Second summer/difference block 1433 generates an error signal and communicates this signal to voltage controlled oscillator 1431. Voltage controlled oscillator 1431 outputs a changed frequency to an input of variable gain amplifier 1416. Now having two inputs, variable gain amplifier 1416 outputs a voltage to power amplifier 1417 which then delivers power to isolating secondary transformer 1436. Isolating secondary transformer 1436 delivers power through second coupling capacitor 1437 and compensating inductor 1438 to ultrasonic transducer 1439.

Simultaneous with delivering power from power amplifier 1417 to isolated transducer circuit 1414, the voltage and current waveforms are communicated (in parallel with isolating secondary transformer 1436) to power monitor 1419 and to phase detector 1432. The average power DC signal is received by first summer/difference block 1425 and compared against the existing power command provided at power command signal input 1426. An error signal is then communicated from first summer/difference block 1425 to power loop controller 1415. Similarly, the phase angle from phase detector 1432 is communicated to second summer/difference block 1433 and compared against phase command signal input 1434 and communicated to frequency loop controller 1430. Power loop and frequency loop controllers, 1415 and 1430 respectively, thereafter send corrective signals to variable gain amplifier 1416, and variable controlled oscillator 1431 as described above.

It should be noted that the phase command signal is more likely than not a non-zero phase command because the final phacoemulsification probe system 1411 is very likely not exactly a purely resistive circuit. The reason that the system 1411 is very likely not a purely circuit is because compensating inductor 1438 has a fixed value which has a slight tolerance variation from unit to unit, and because the parallel capacitance of transducer 1439 may vary from handpiece to handpiece, and because environmental factors could cause the resonant frequency of ultrasonic transducer 1439 to change. For this reason, it also very likely that the optimal phase angle Φ for a particular power level is also non-zero. When the phase angle Φ is zero, the circuit is purely resistive. If there is an imbalance in the circuit, the phase angle cannot be zero because the circuit is not purely resistive. However, on average it is estimated that the optimal phase angle will generally be within at least twenty degrees of zero.

Figure 11:
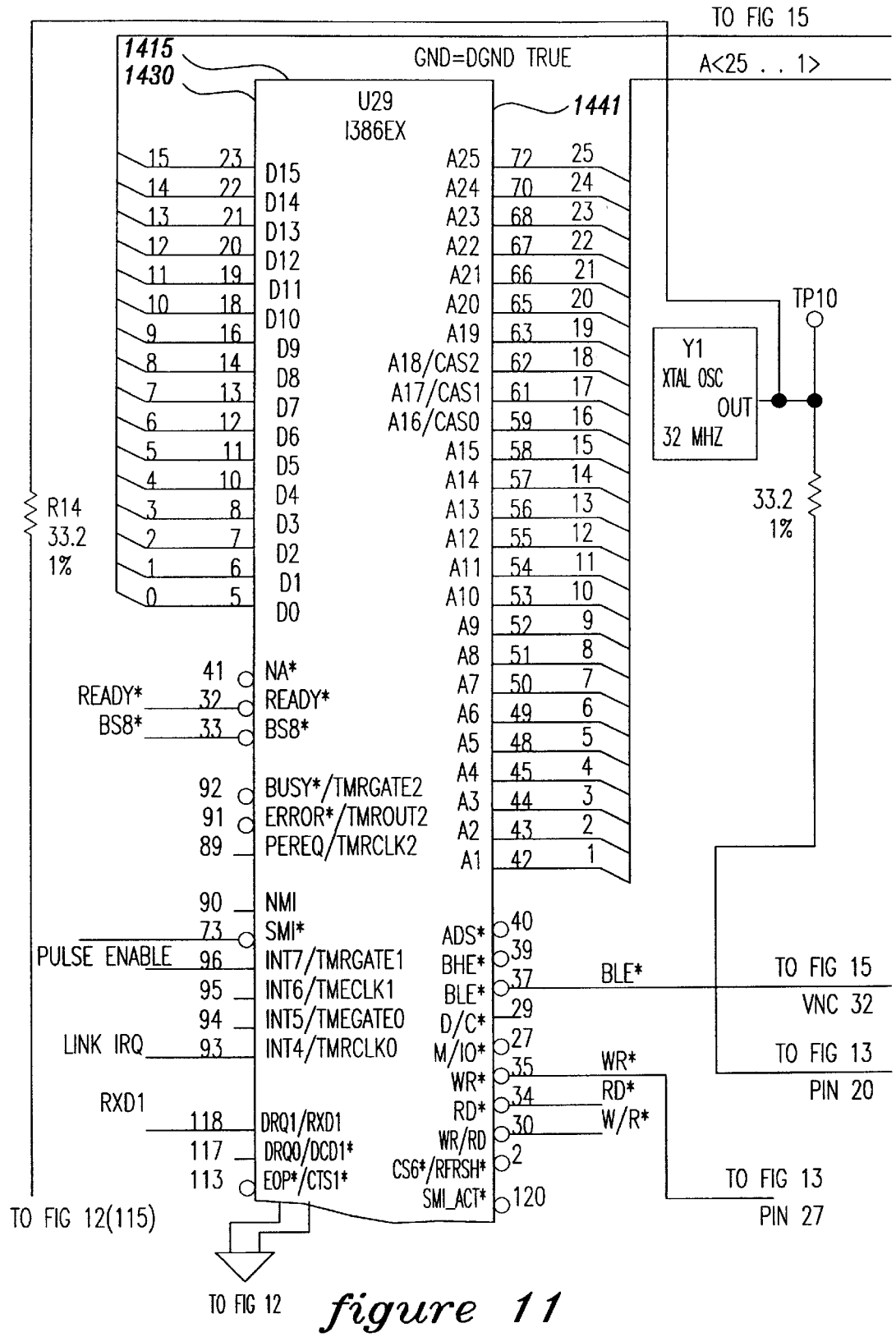
FIGS. 11, 12, 13, 14 and 15 illustrate a hardware-implemented embodiment of the present invention depicting a coprocessor and an electronically programmable logic device.
Figure 12:
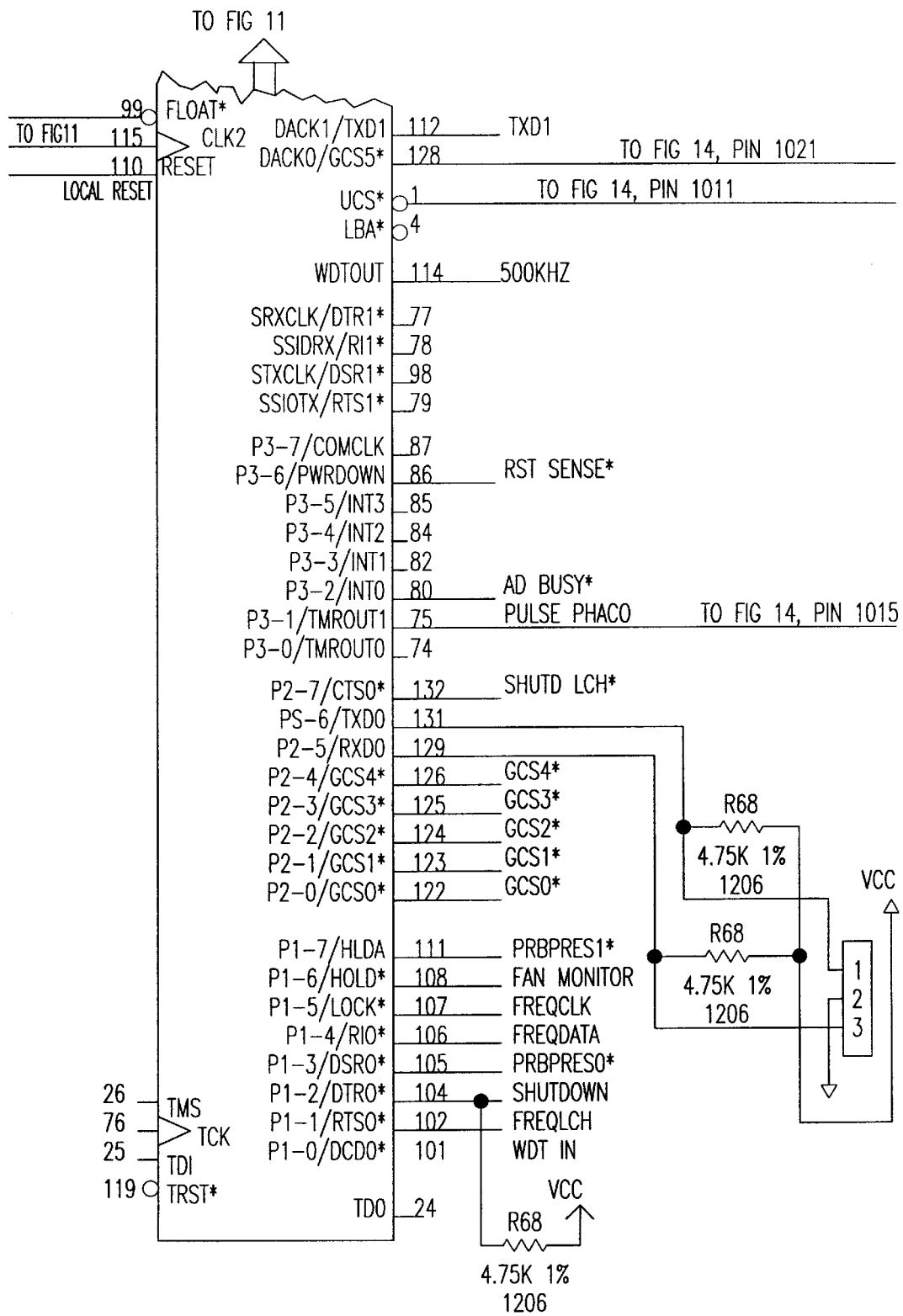
Figure 13:
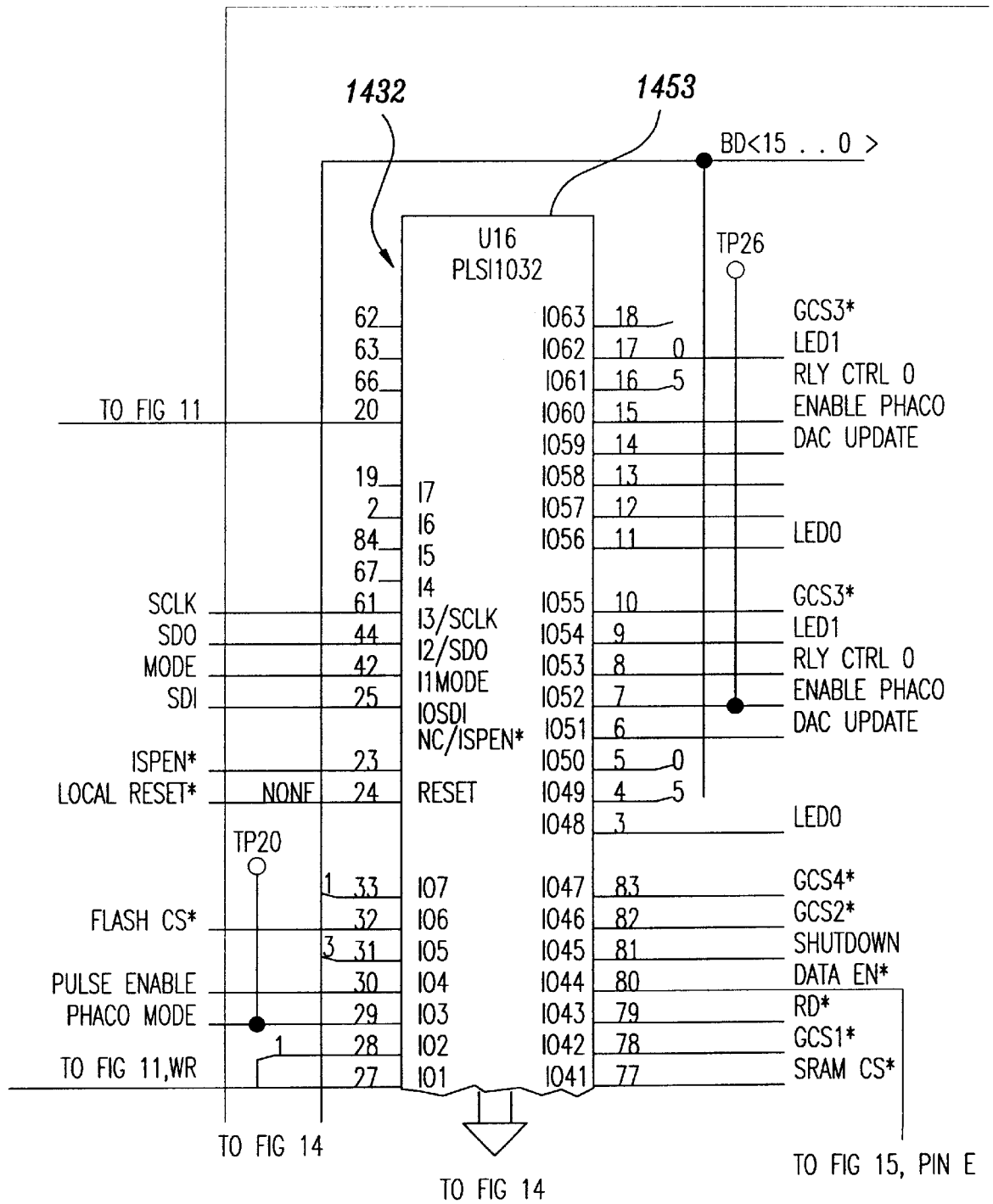
Figure 14:
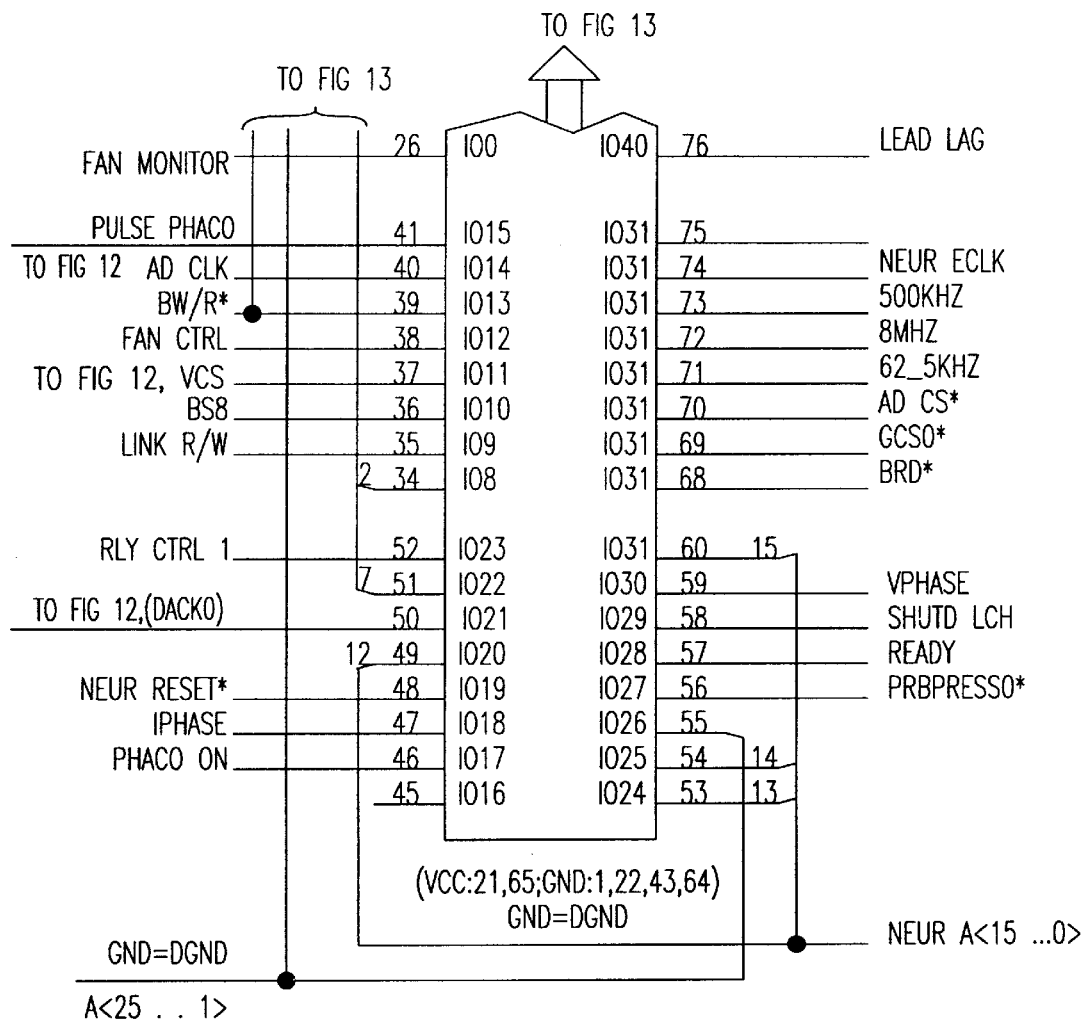
Figure 15:
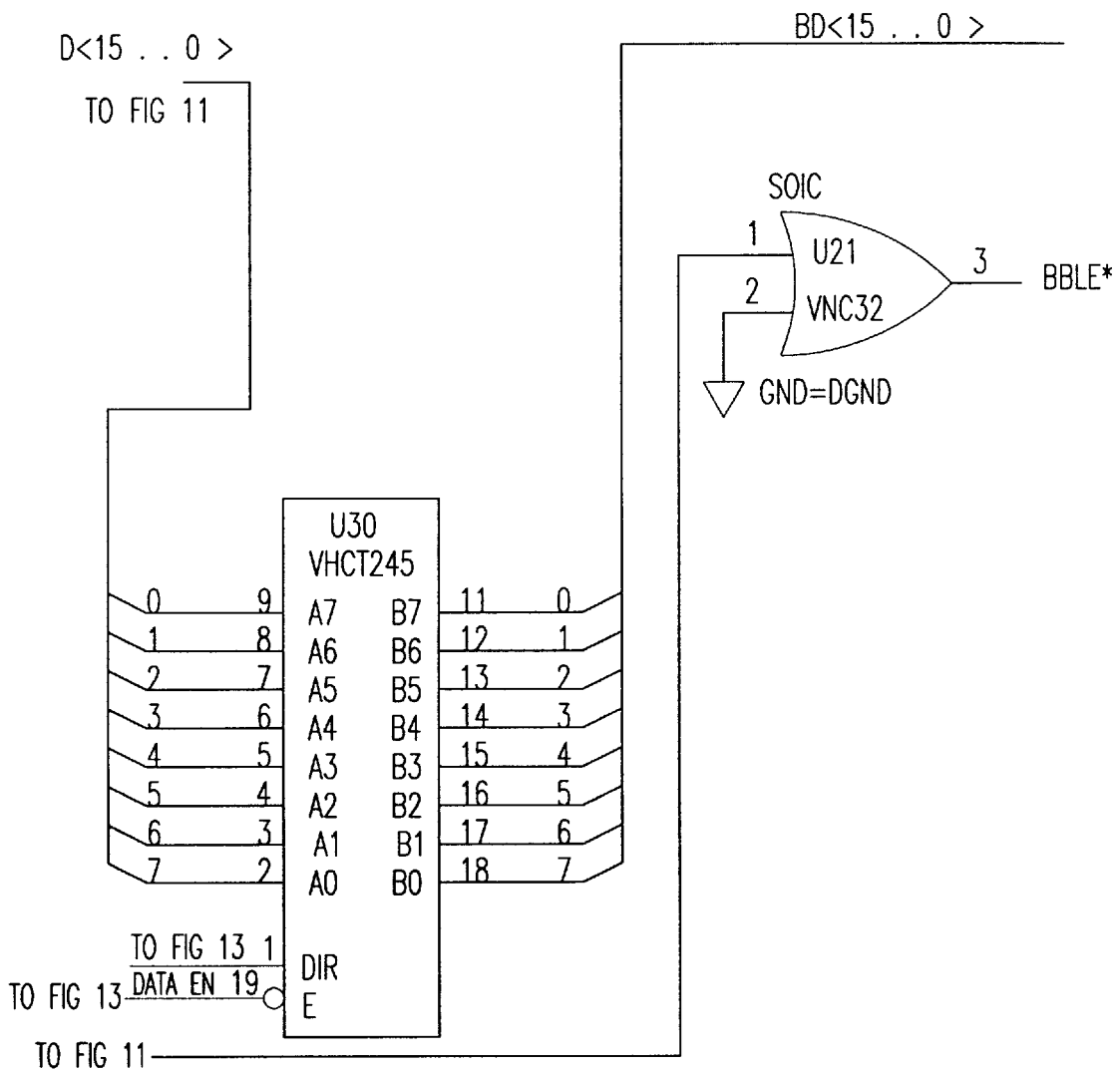
Figure 16:
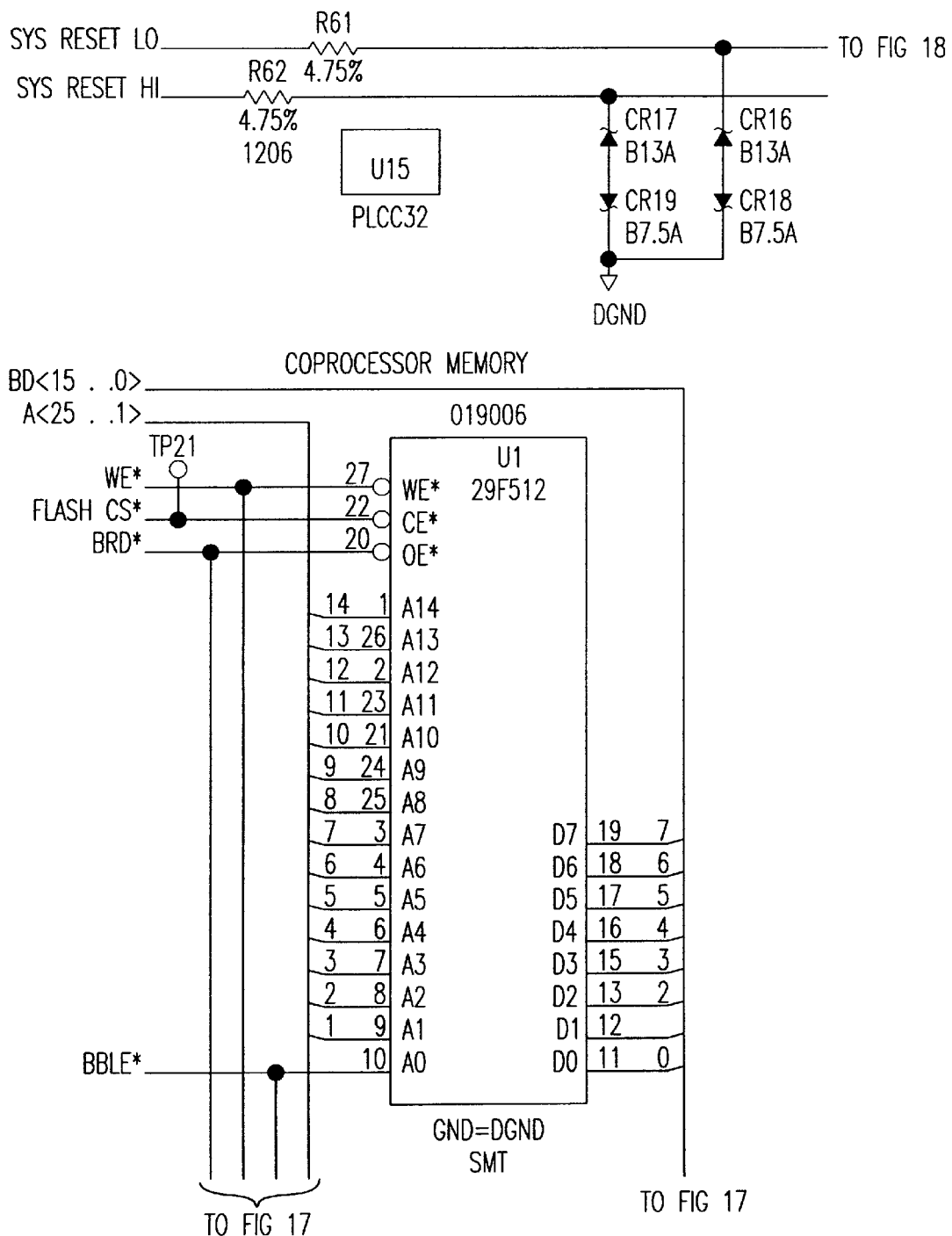
FIGS. 16, 17, 18 and 19 illustrate a hardware-implemented embodiment of the present invention depicting memory for the coprocessor and a reset circuit.
Figure 17:
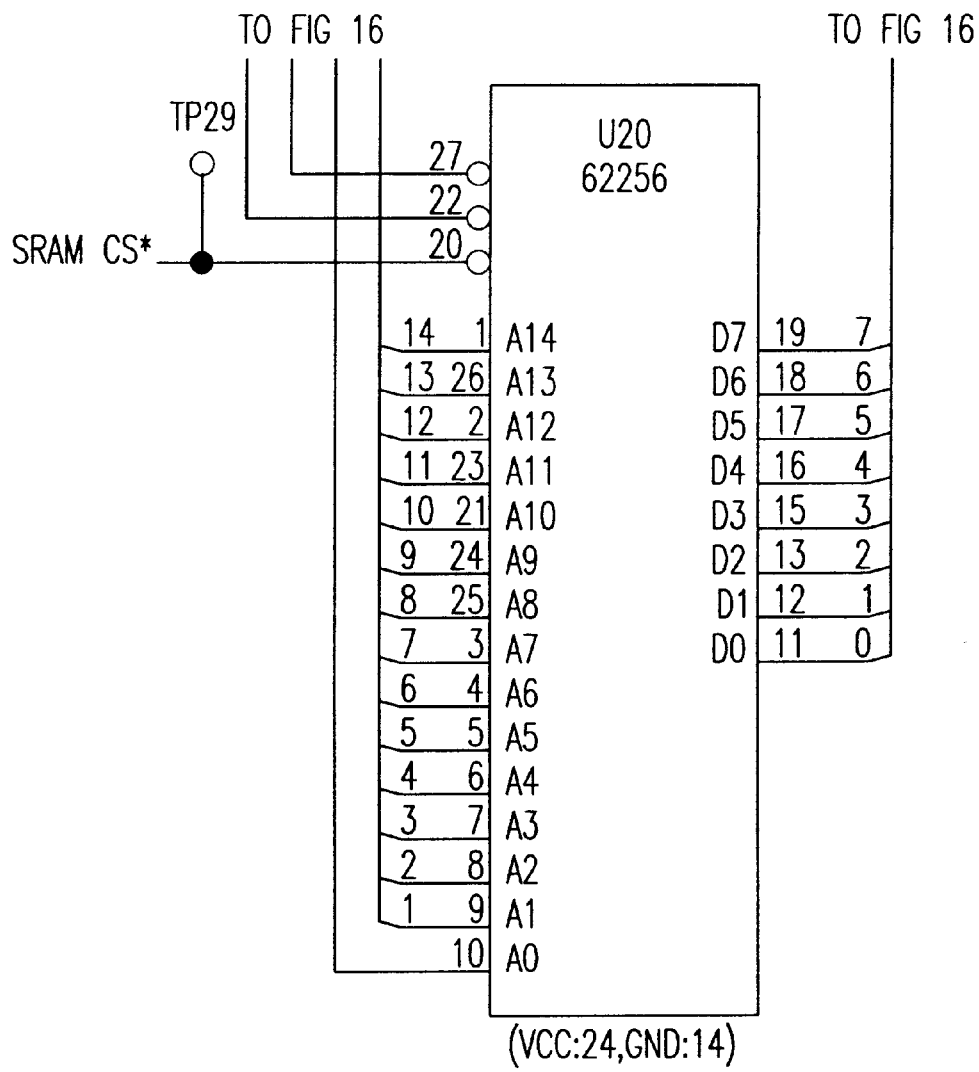
Figure 18:
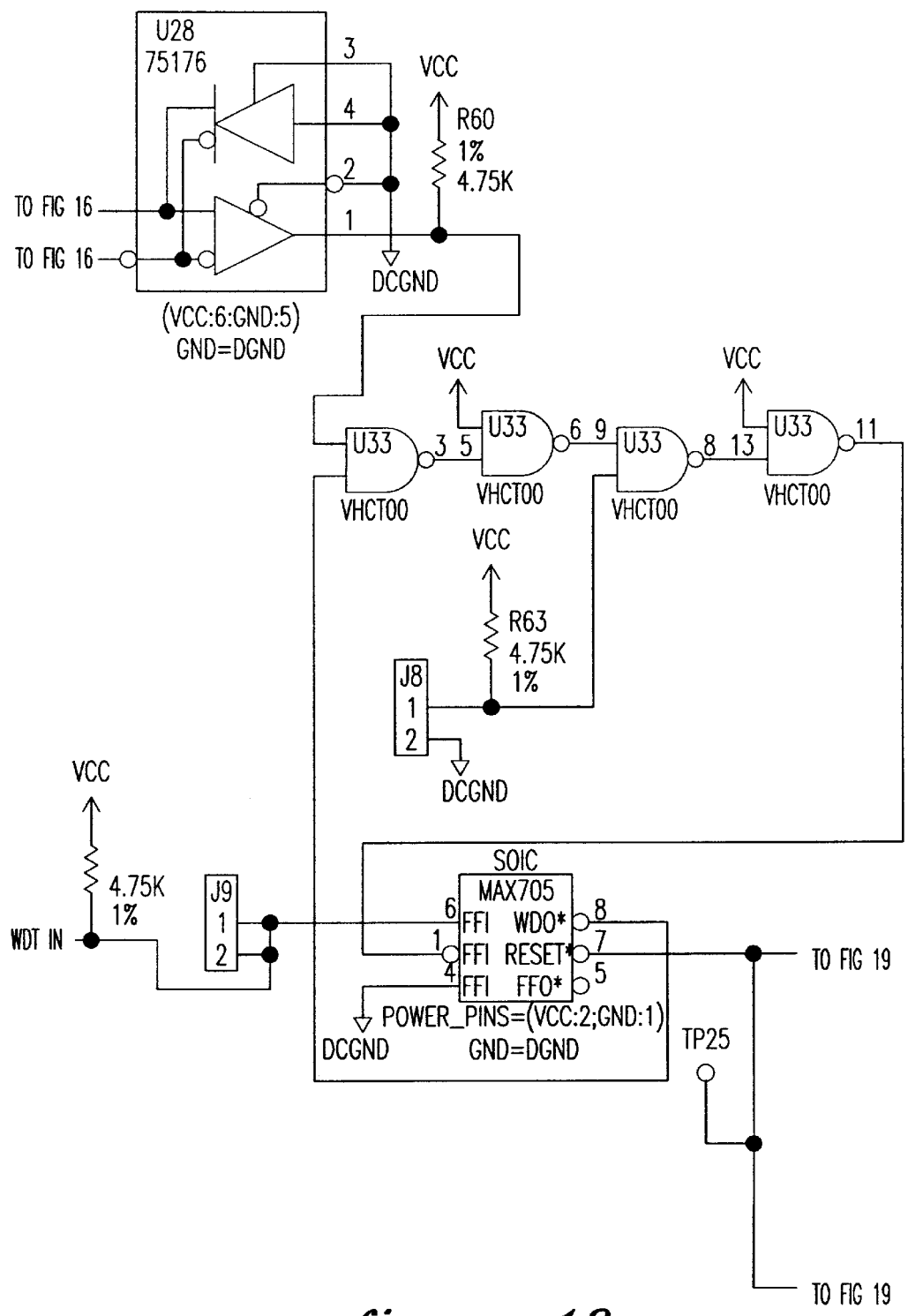
Figure 19:
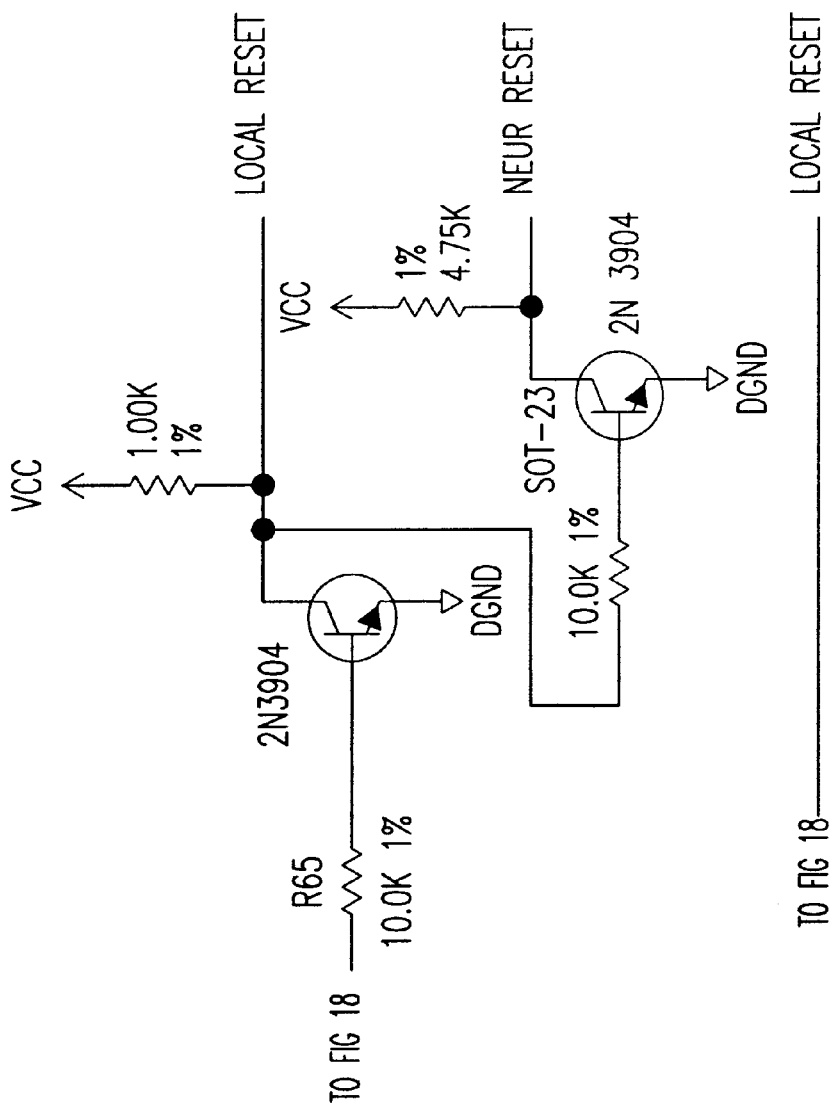
Figure 23:
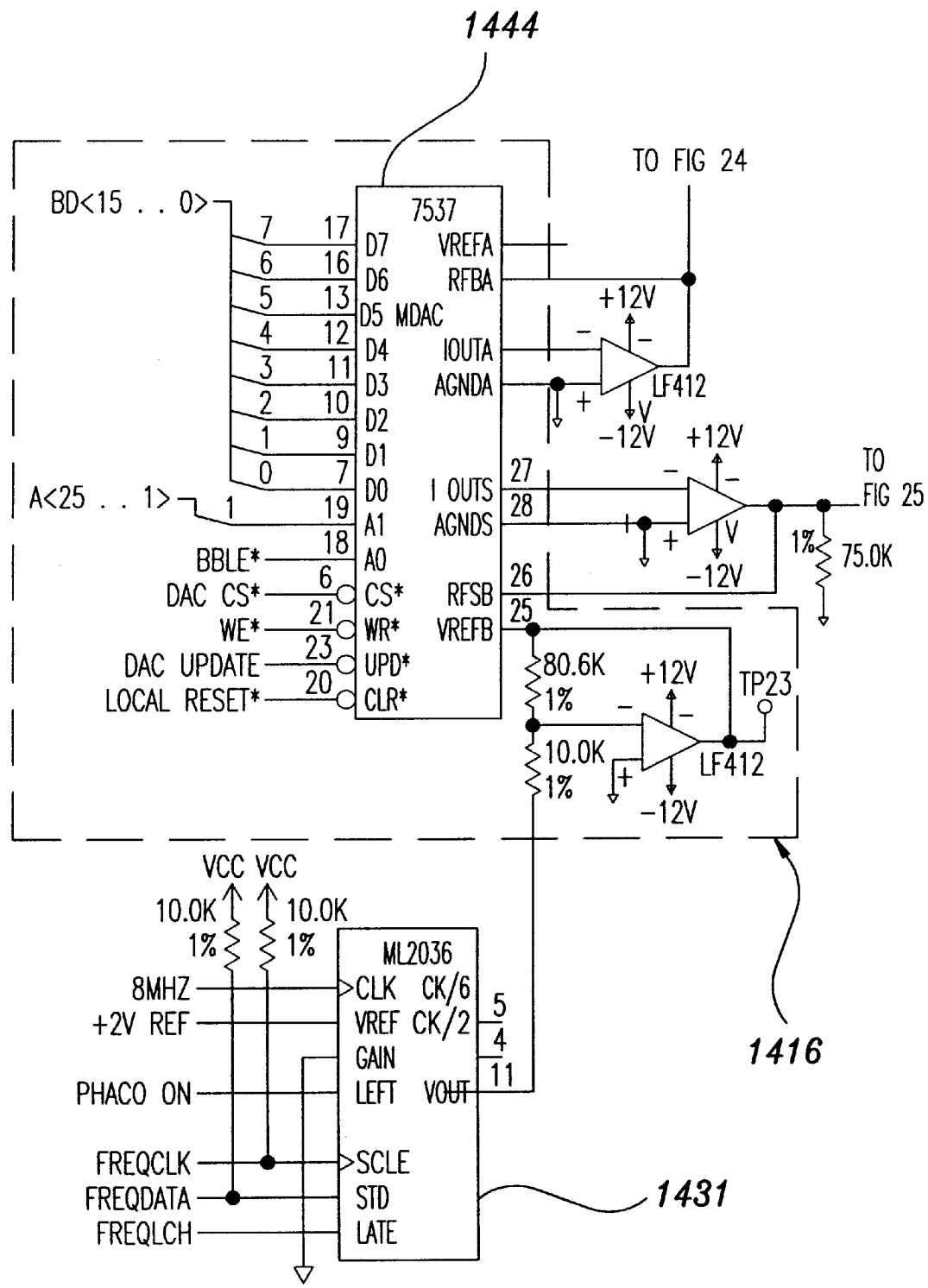
FIGS. 23, 24 25 and 26 illustrate a hardware-implemented embodiment of the present invention depicting a boost regulator, a voltage controlled oscillator, a multiplying digital to analog converter, a variable gain amplifier, a power amplifier, a first coupling capacitor, an isolating transformer, a second coupling capacitor, a compensating inductor, and an ultrasonic transducer.
Figure 24:
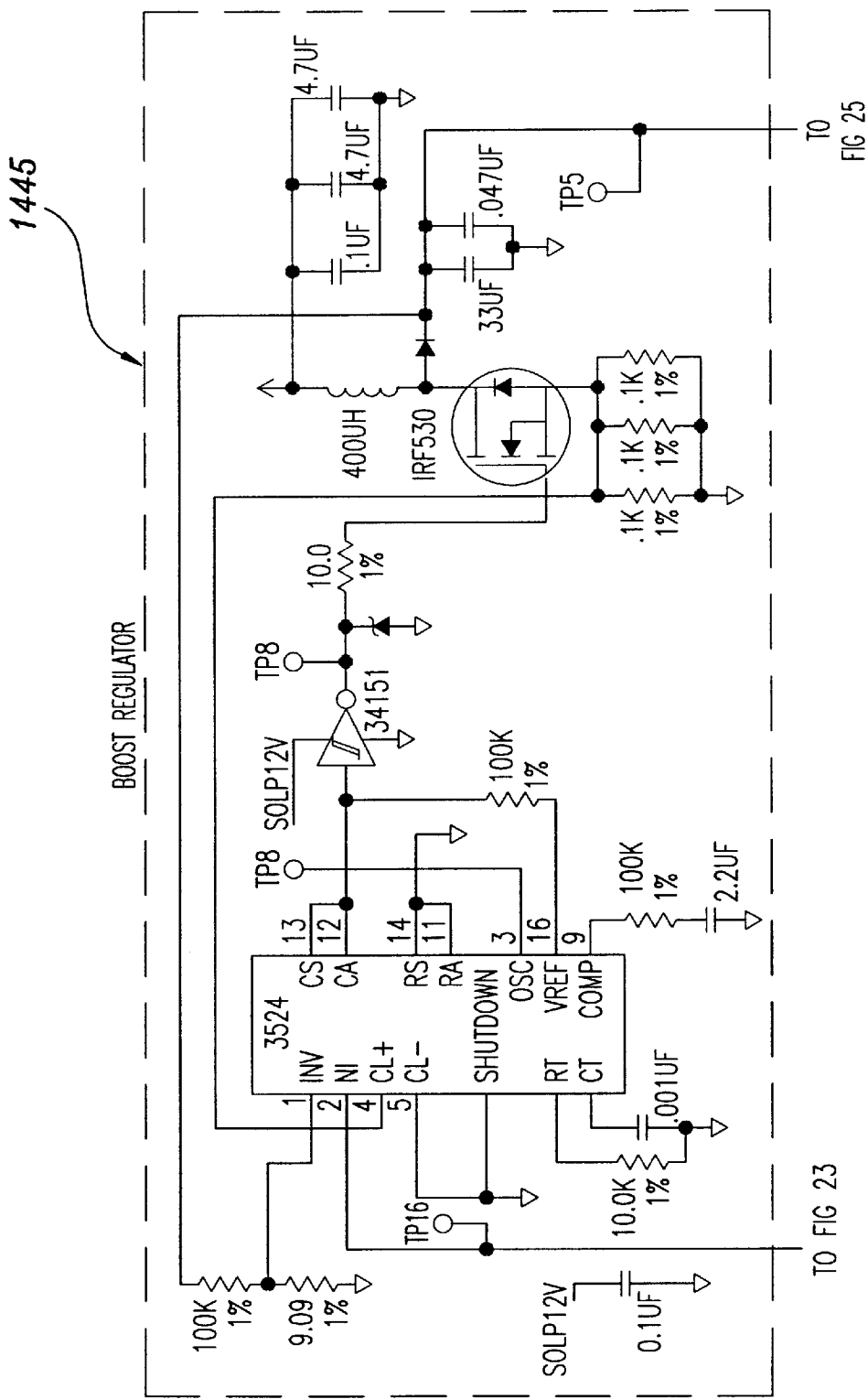

FIGS. 11–32 are provided first to simply enable the reader to prepare detailed circuit schematics of the block diagram shown in FIG. 8, and second to reveal the best mode of practicing the invention. The functions of power loop controller 1415 and frequency loop controller 1430 are physically combined in hardware into one coprocessor 1441 shown in FIGS. 11 and 12. The coprocessor 1441 of FIGS. 11 and 12 is connected to the voltage control oscillator 1431 shown in FIG. 23, a sign wave generator, which passes its signal to the variable gain amplifier 1416, embodied in labelled LF 412 in combination with the multiplying digital to analog converter (MDAC), indicated by reference numeral 1444. MDAC 1444 is a two-channel DAC which passes a signal to boost regulator circuit shown in FIG. 24 which provides the power supply and offset voltage to power amplifier 1417 shown in operational amplifier block labeled LM12 in FIG. 25. It is noted that the boost regulator circuit is not required to effect the present invention. A boost regulator circuit is simply a different means for providing the supply voltage to power amplifier 1417, and use of the circuit requires an additional controller to calculate the required boost voltage output and to send a boost command to the boost regulator.

Figure 25:
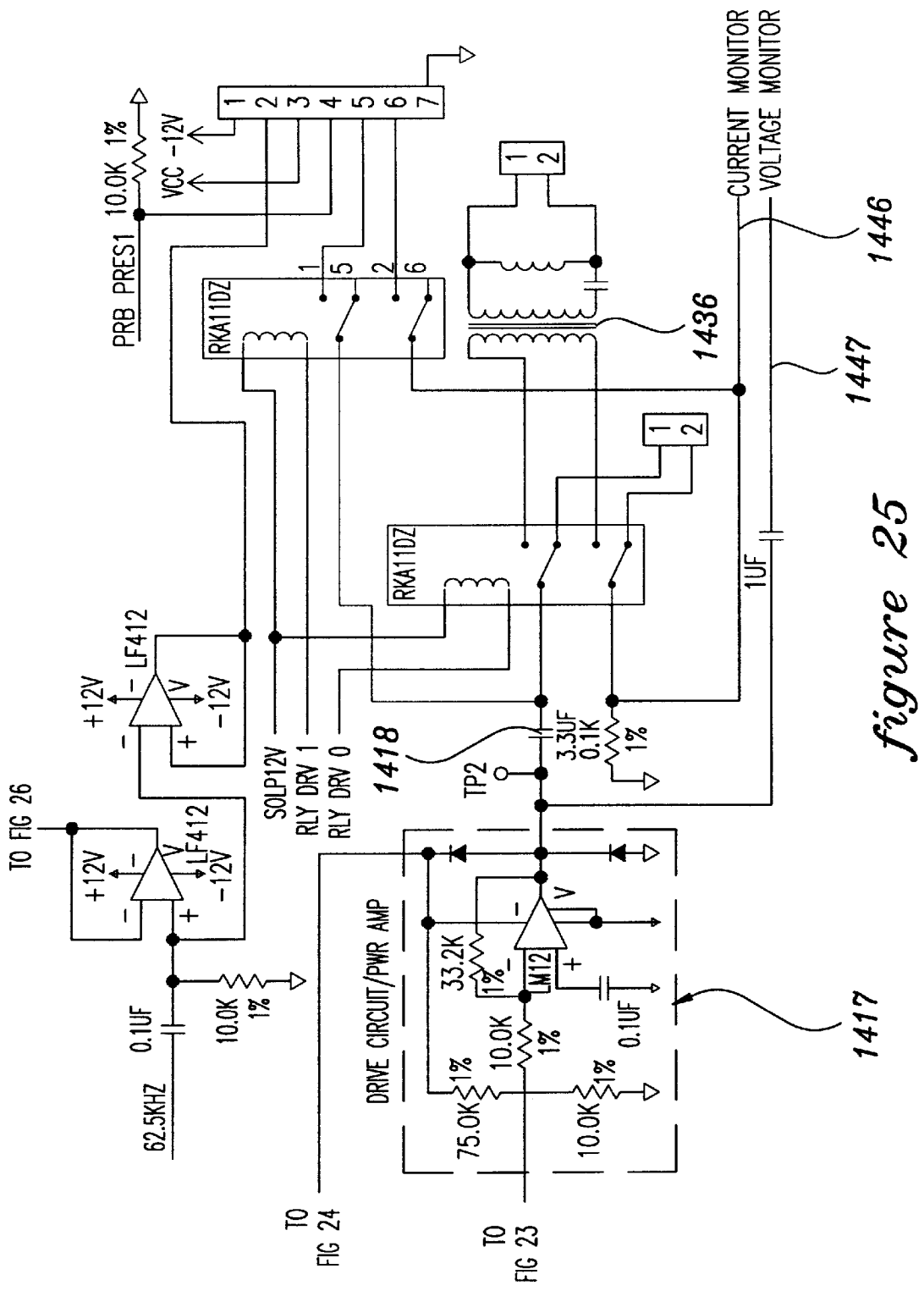
Figure 26:
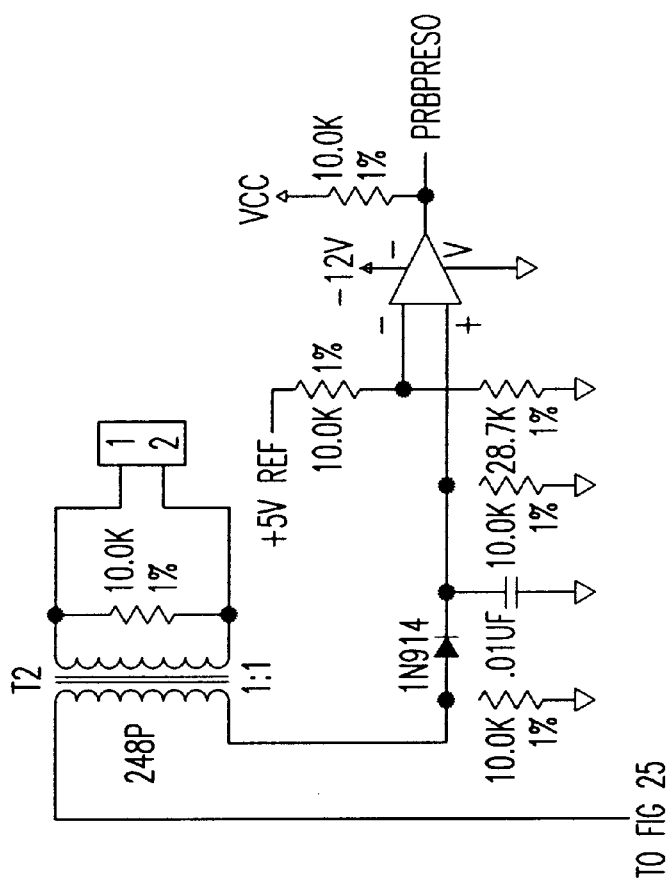

The output from power amplifier 1417 is passed through coupling capacitor 1418 and thence to isolating transformer 1436. As shown on the rightmost portion of FIG. 25, current monitor lead 1446 and voltage monitor lead 1447 are provided to sense the current and voltage delivered to isolating transformer 1436. The monitor leads, 1446 and 1447 respectively, from FIG. 25 are continued onto FIG. 27 wherein the monitor signals are scaled by operational amplifier blocks labelled LF412 having numerical reference numerals 1448 and 1449.

After scaling, the power monitor 1419 senses the power delivered to first transformer (primary transformer) 1436. Specifically, voltage RMS to DC converter 1420 is shown in block AD536 and current RMS to DC converter 1421 is shown in similarly labelled block AD536. Thereafter, the outputs are communicated to an analog to digital converter shown in block MAX182 (numbered 1450) which converts the sine wave signal to DC and thence to the coprocessor 1441 shown in FIG. 11.

Figure 27:
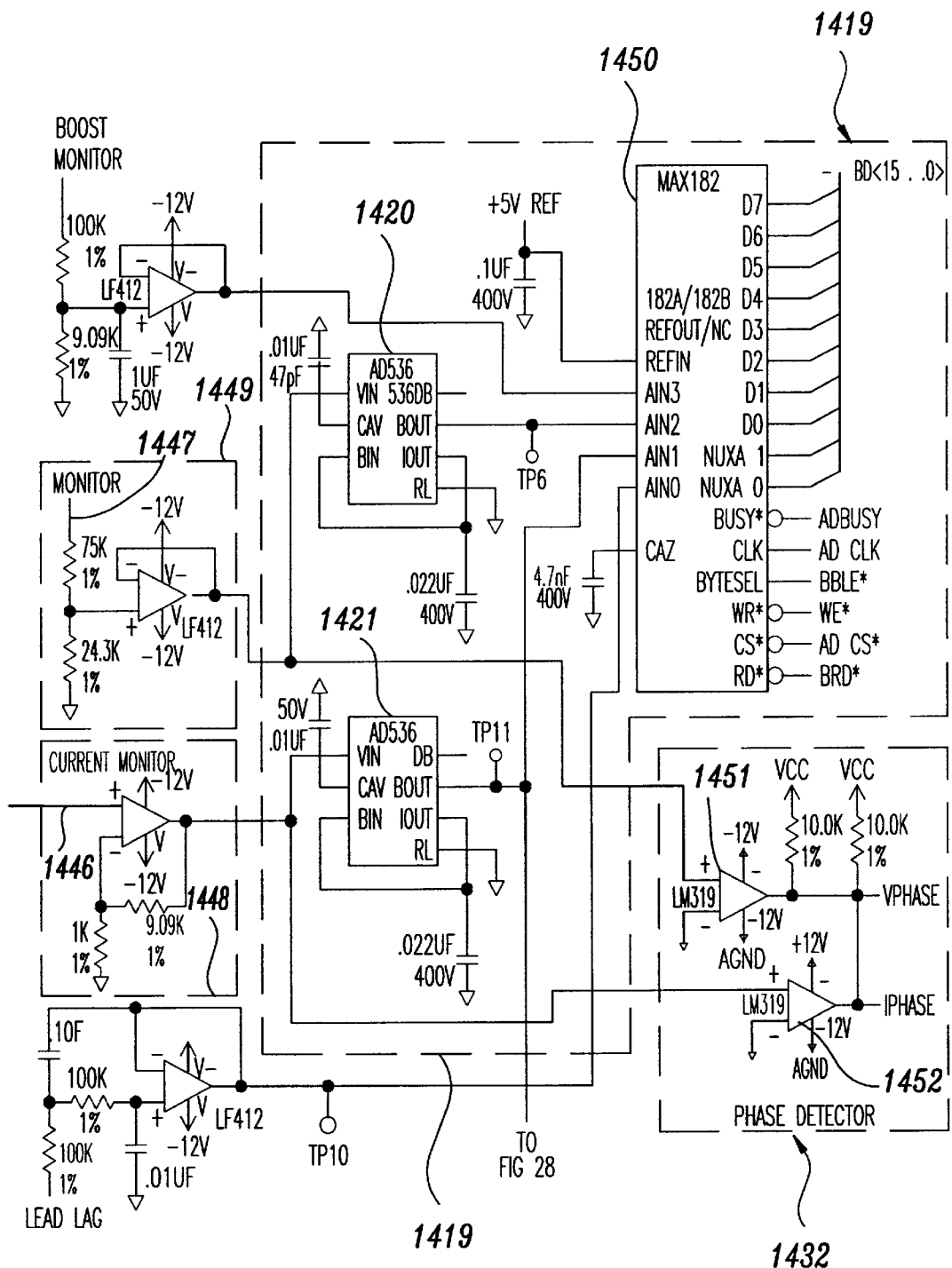
FIGS. 27 and 28 illustrate a hardware-implemented embodiment of the present invention depicting voltage and current RMS to DC converters, and an average power detector.
Figure 28:
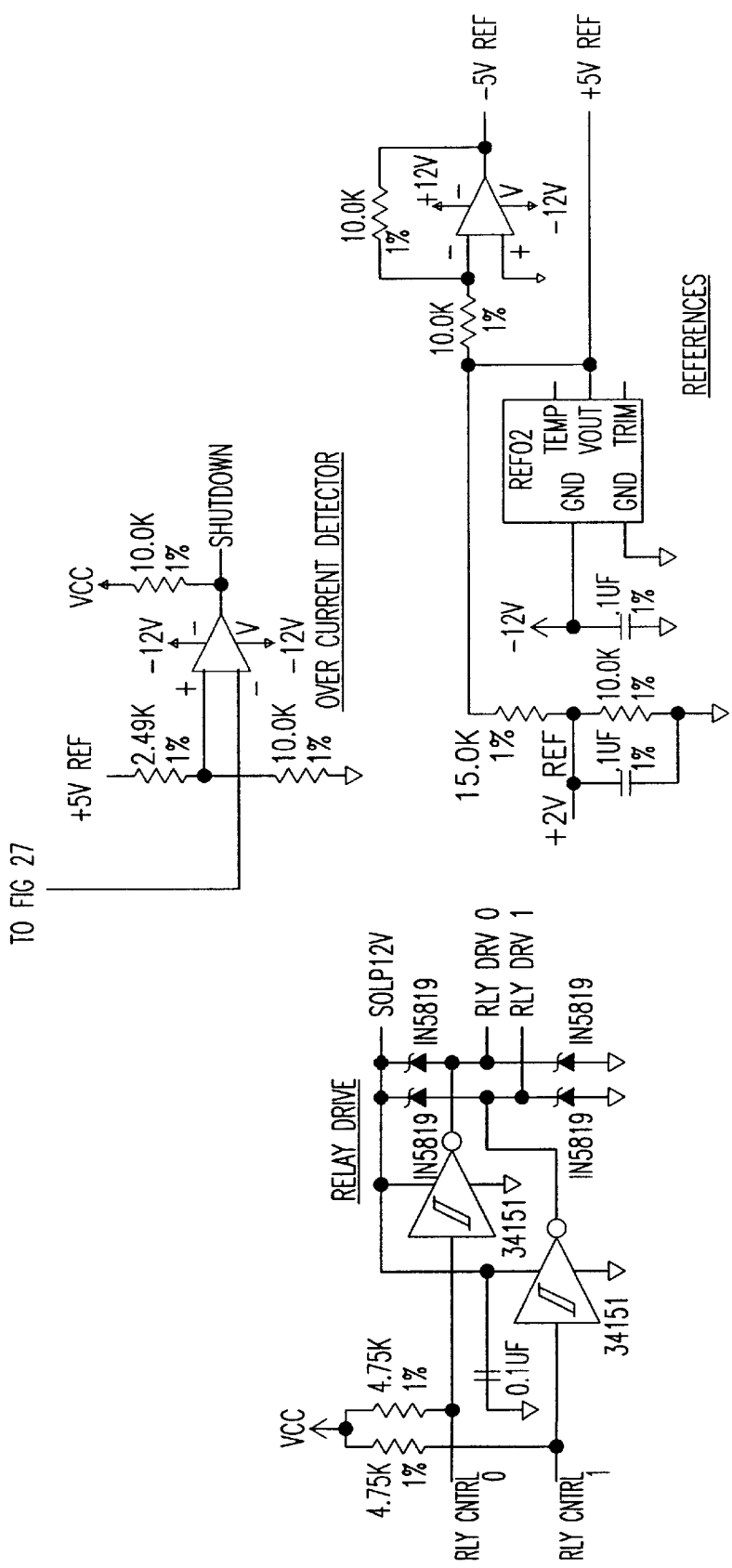
Figure 29:
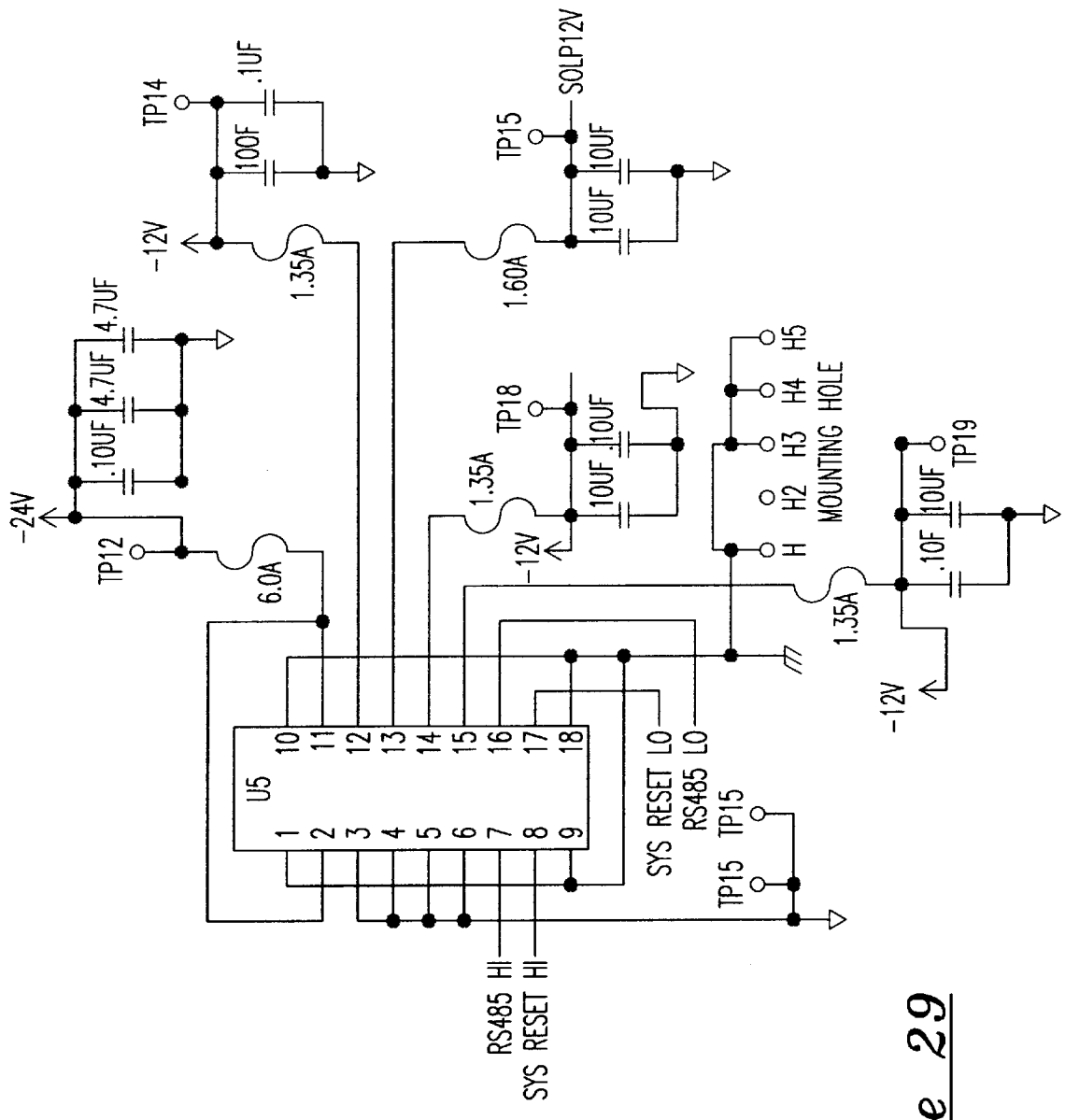
FIGS. 29 and 30 illustrate a hardware-implemented embodiment of the present invention depicting various minor hardware aspects.
Figure 30:
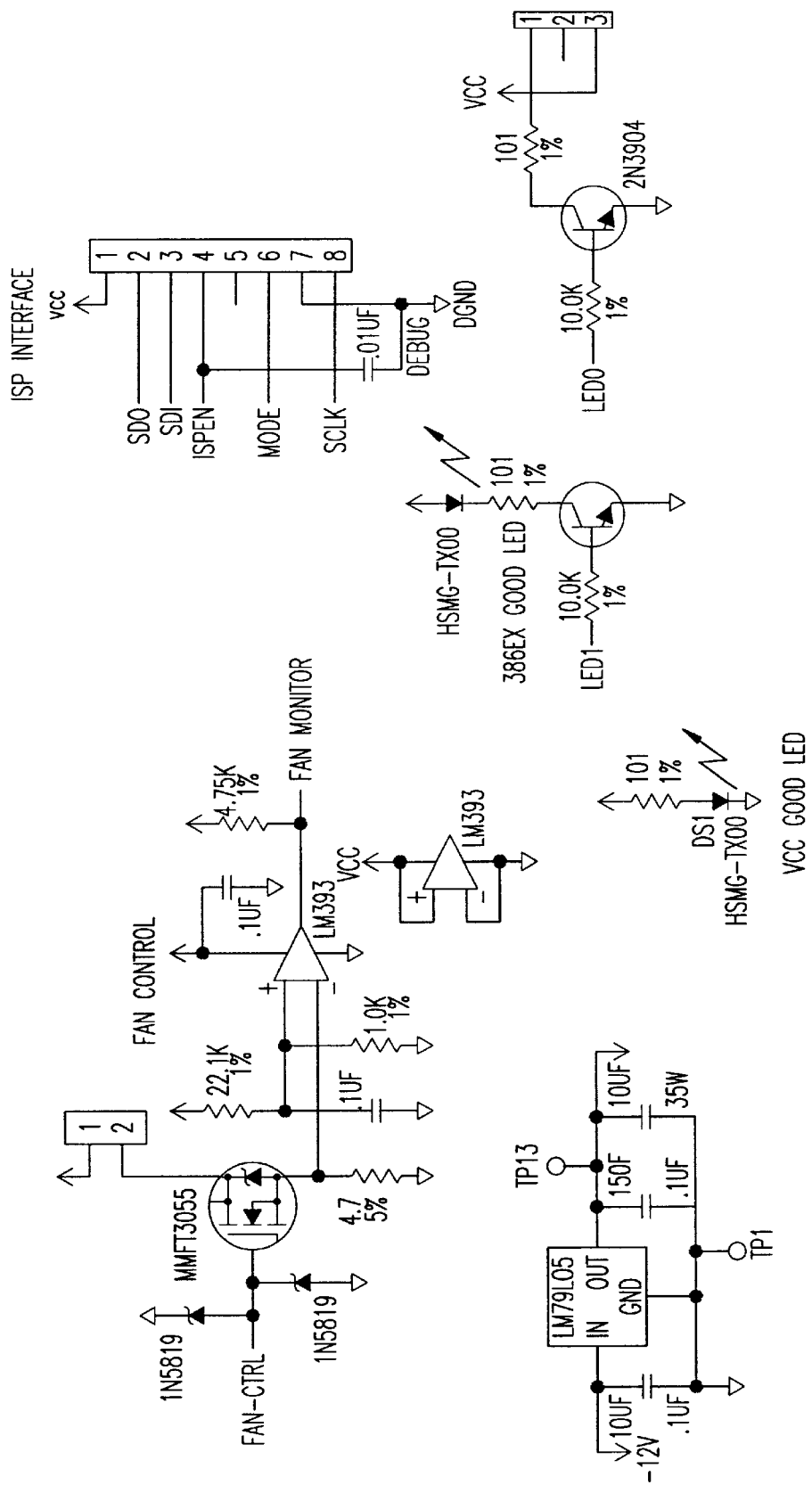
Figure 31:
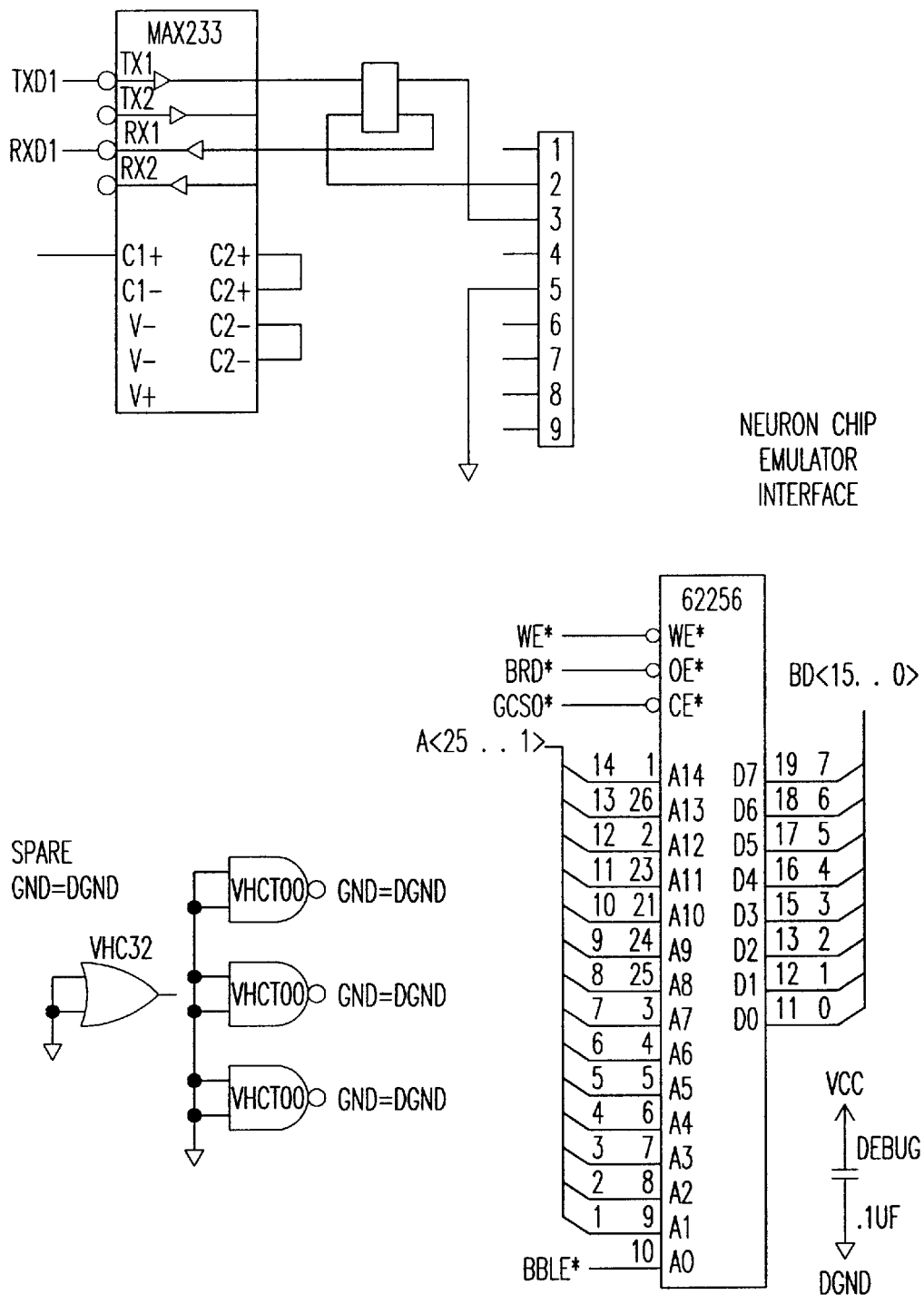
FIGS. 31 and 32 illustrate a hardware-implemented embodiment of the present invention depicting various minor hardware aspects.
Figure 32:
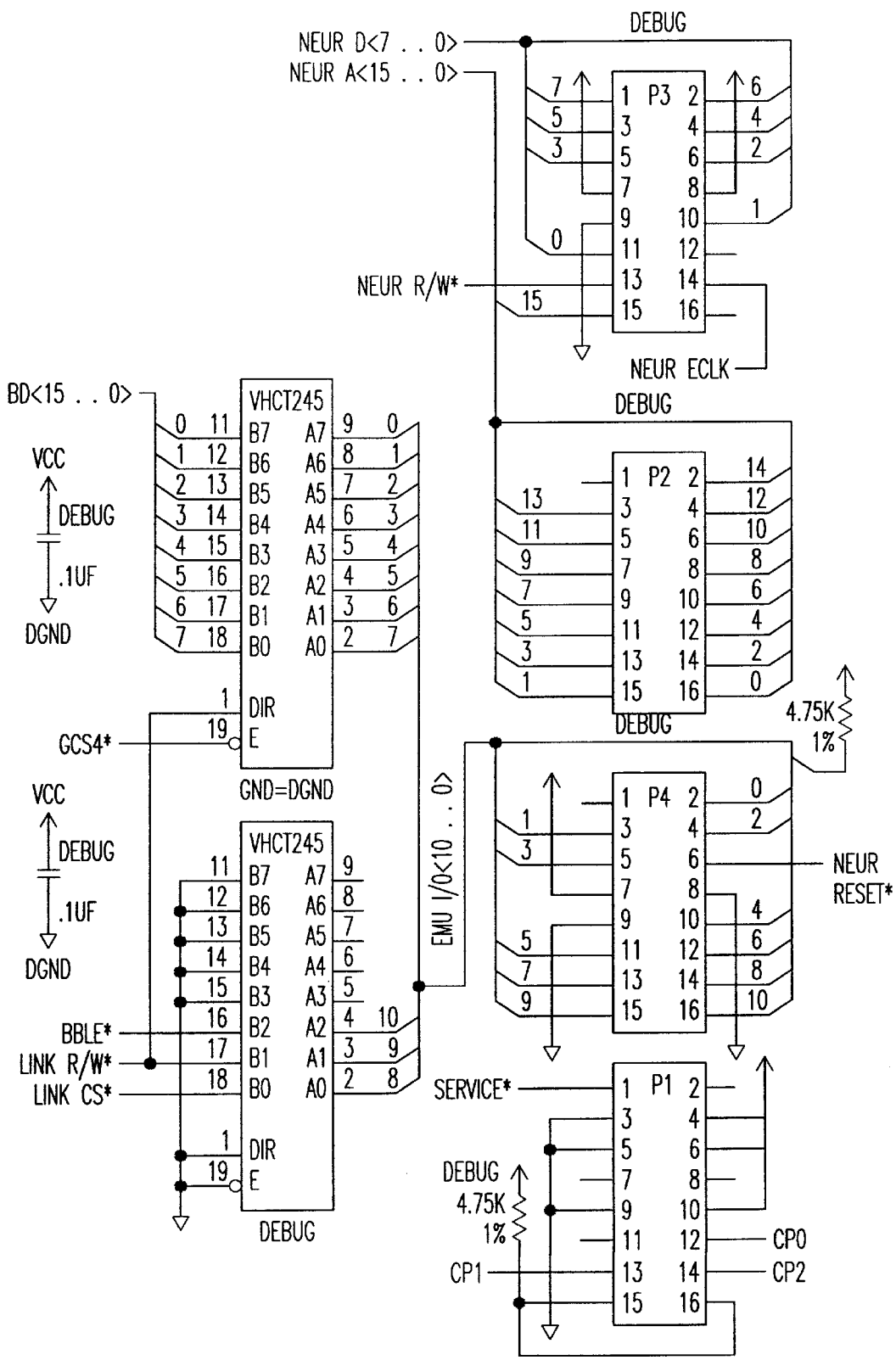

In FIG. 27, after the voltage and current monitors, 1446–1447, are scaled, they also communicate with the phase detector 1432 which is comprised of two parts: (1) the zero crossing detector operational amplifier shown in blocks labelled LM319 (numbered 1451 and 1452) in FIG. 27; and (2) thence to FIG. 13 to the Electronically Programmable Logic Device (EPLD) 1453 shown in block PLSI1032. Upon leaving the EPLD 1453 in FIG. 13, the output is transmitted to FIG. 27, the lead lag low pass filter shown in block LF412 and thence to the analog to digital converter 1450 shown in block MAX182, and then to coprocessor 1441 shown in FIG. 11.

Figure 20:
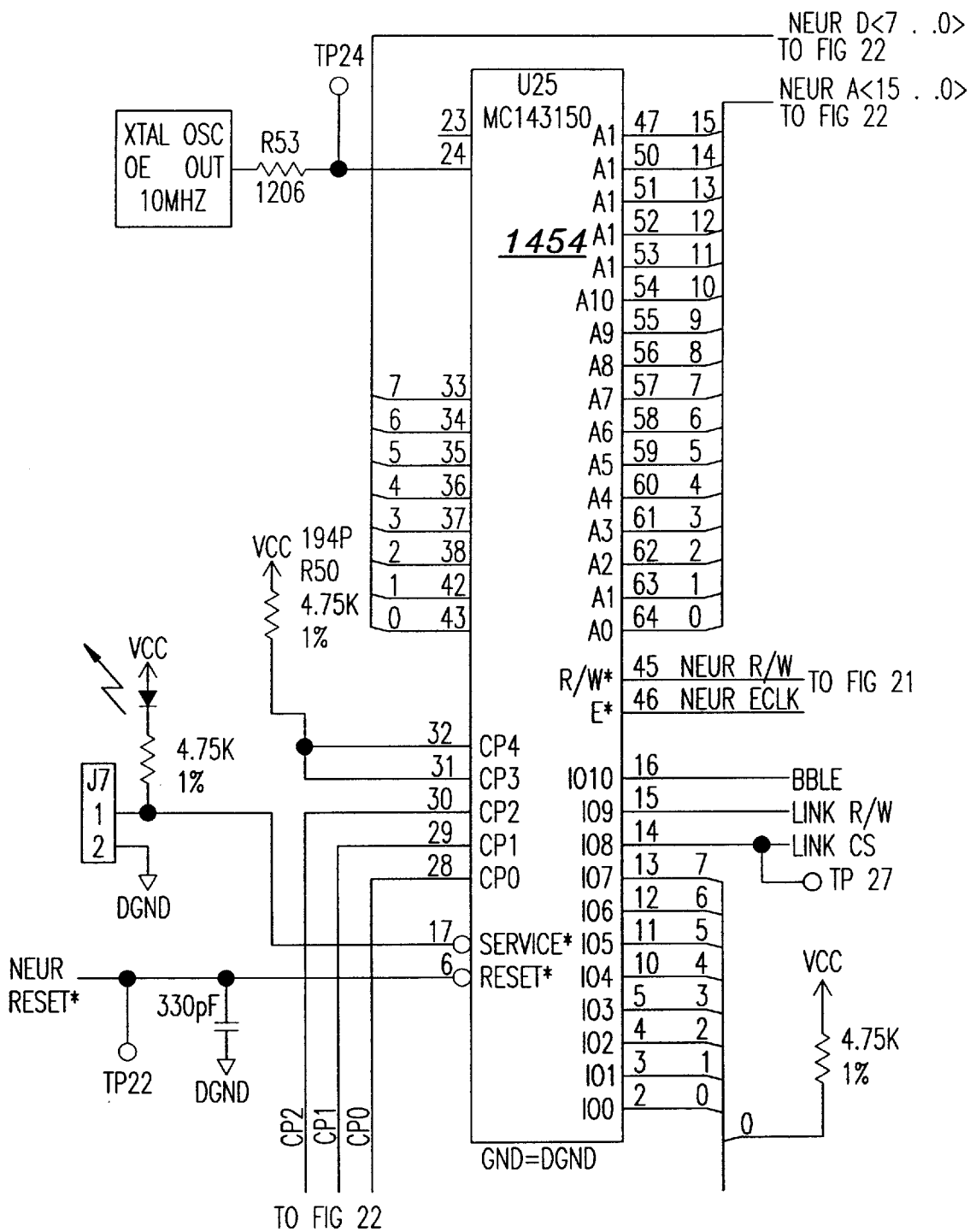
FIGS. 20, 21 and 22 illustrate a hardware-implemented embodiment of the present invention depicting a transceiver, and a neuron integrated circuit chip.
Figure 21:
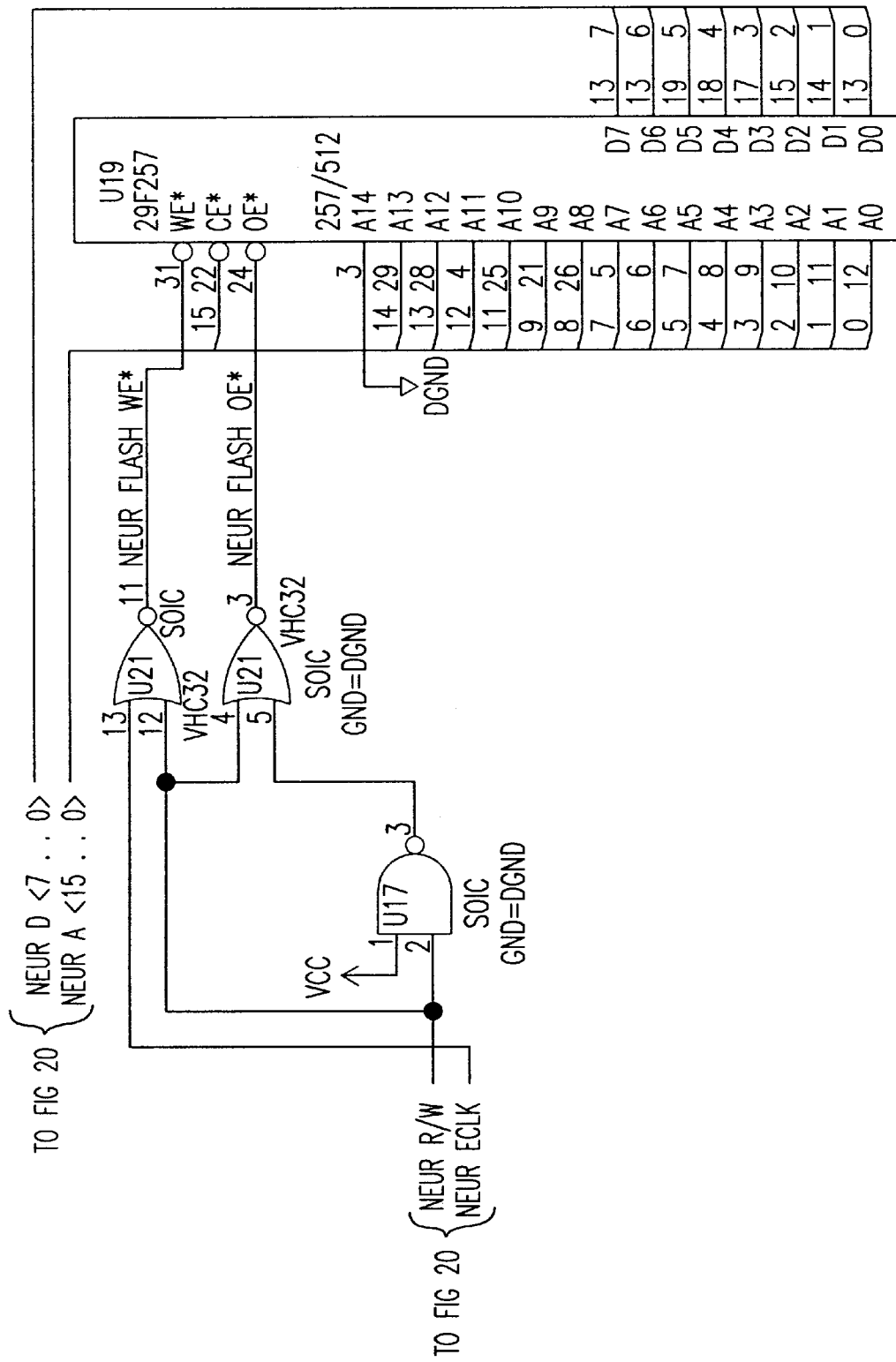
Figure 22:
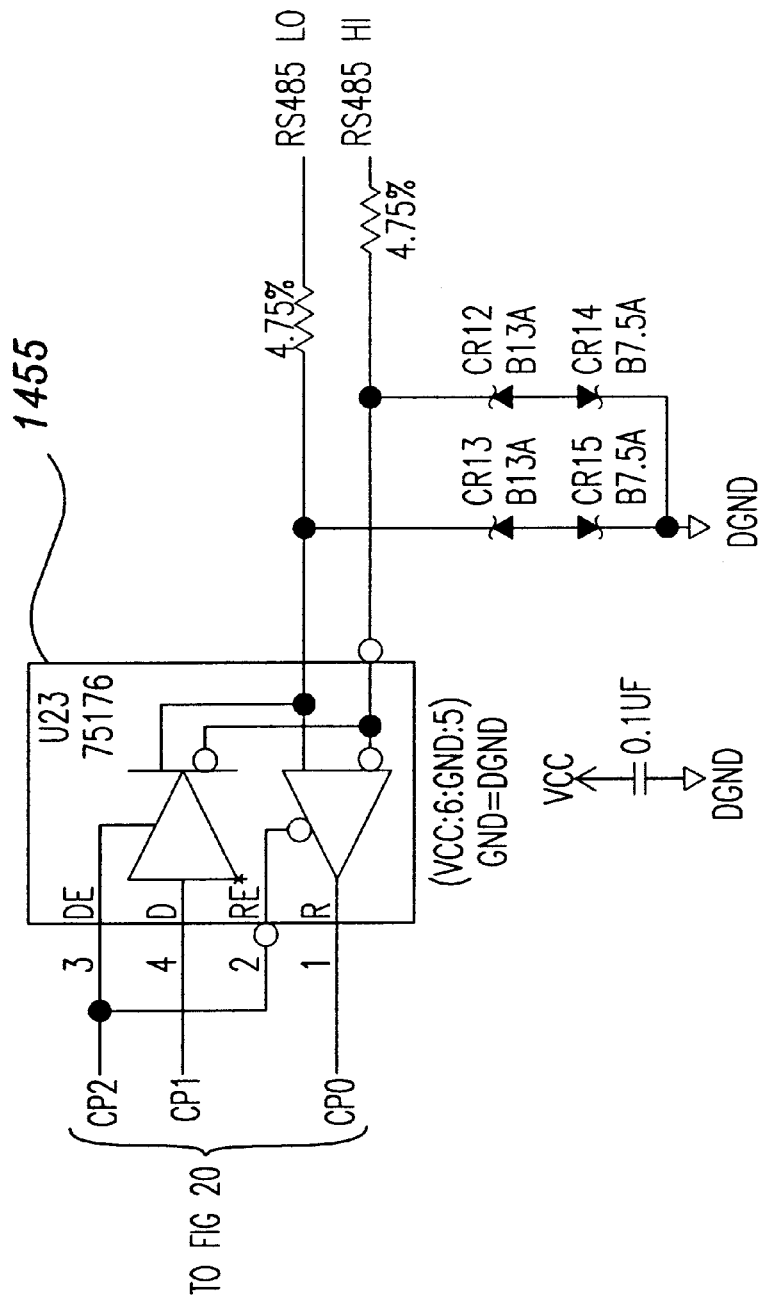

Turning to FIG. 20, a NEURON chip 1454 (NEURON is a registered trademark) is shown in block U25. This chip has the following function. When the surgeon depresses the foot control, a communication from the foot control is transmitted transceiver 1455 shown in FIG. 22 block U23. Once the power command communication is received by transceiver 1455, it is sent to NEURON chip 1454 in block U25, and then to the coprocessor 1441 shown in FIG. 11.

In view of the foregoing, it will be seen that the several objects of the invention are achieved and other advantages are attained. The embodiments were chosen and described in order to best explain the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. For example, the hardware implementation of the present invention may be changed by consolidation or expansion with other hardware, or may be replaced with software. In another example, the power amplifier may obtain an additional input from a boost regulator which can provide a power supply and an offset voltage with departure from the spirit of the present invention. Specifically, upon receipt of an error signal in the compared power values, the power loop controller may send a signal to the third controller which then applies an input to the boost regulator whose output becomes one input for the power amplifier. Thus, the breadth and scope of the present invention should not be limited by any of the above-described exemplary embodiments, but should be defined only in accordance with the following claims appended hereto and their equivalents.

What is claimed is:

1. A circuit for a phacoemulsification probe system comprising:

a frequency loop controller having an output connected to an input of a voltage controlled oscillator;

a power loop controller having an output connected to an input of a variable gain amplifier;

said voltage controlled oscillator having an output connected to an input of said variable gain amplifier;

a power amplifier connected to an output of said variable gain amplifier;

said power amplifier delivering power including voltage and current waveforms to an isolated power transformer;

a power monitor connected to and sensing said power delivered to said isolated power transformer;

a power summer having an input connected to an output of said power monitor, and having an output connected to said power loop controller;

a phase detector connected to and sensing said voltage and current waveforms delivered to said isolated power transformer; and a phase summer having an input connected to an output of said phase detector, and having an output connected to said frequency loop controller.

2. A circuit for a phacoemulsification probe system according to claim 1, wherein said power monitor comprises:

a voltage RMS to DC converter connected to and sensing the voltage waveform delivered to said isolated power transformer;

a current RMS to DC converter connected to and sensing the current waveform delivered to said isolated power transformer;

a multiplier having one input connected to said voltage RMS to DC converter and another input connected to said current RMS to DC converter, and having an output connected to said power summer.

3. A circuit for a phacoemulsification probe system according to claim 1, wherein said power monitor comprises:

a multiplier having one input connected to and sensing the voltage waveform delivered to said isolated power transformer and another input connected to and sensing the current waveform delivered to said isolated power transformer; and a low pass filter having an input connected to an output of said multiplier, and having an output connected to said phase summer.

* * * * *